(12) United States Patent
Artursson et al.

(10) Patent No.: US 7,767,456 B2
(45) Date of Patent: *Aug. 3, 2010

(54) NON-VIRAL GENE DELIVERY SYSTEM

(75) Inventors: Per Artursson, Uppsala (SE); Bjorn Erik Christensen, Trondheim (NO); Magnus Koping-Hoggard, Uppsala (SE); Kjell Morten Varnum, Trondheim (NO)

(73) Assignee: FMC Biopolymer AS, Drammen (NO)

( * ) Notice: Subject to any disclaimer, the term of this patent is extended or adjusted under 35 U.S.C. 154(b) by 392 days.

This patent is subject to a terminal disclaimer.

(21) Appl. No.: 11/809,816

(22) Filed: Jun. 1, 2007

(65) Prior Publication Data

US 2007/0298048 A1 Dec. 27, 2007

Related U.S. Application Data

(63) Continuation of application No. 10/513,429, filed as application No. PCT/NO03/00143 on May 2, 2003, now abandoned.

(30) Foreign Application Priority Data

May 3, 2002 (NO) .................................. 20022148

(51) Int. Cl.
- C12N 15/00 (2006.01)
- A01N 43/04 (2006.01)
- C08B 37/08 (2006.01)
- C07H 21/00 (2006.01)

(52) U.S. Cl. .......................... 435/455; 514/44; 514/55; 536/20; 536/23.1

(58) Field of Classification Search .................. 435/455; 514/44, 55; 536/20, 23.1
See application file for complete search history.

(56) References Cited

U.S. PATENT DOCUMENTS

| 5,972,707 | A | 10/1999 | Roy et al. |
| 6,184,037 | B1 | 2/2001 | Rolland et al. |
| 6,316,007 | B1 | 11/2001 | Nordquist et al. |
| 2001/0031497 | A1 | 10/2001 | Rolland et al. |

FOREIGN PATENT DOCUMENTS

| EP | 0 994 726 | 4/2002 |
| JP | 3198782 | 6/2001 |
| WO | WO-97/42975 | 11/1997 |
| WO | WO-98/01160 | 1/1998 |
| WO | WO-98/01161 | 1/1998 |
| WO | WO-98/01162 | 1/1998 |
| WO | WO-98/17693 | 4/1998 |
| WO | WO-99/36089 | 7/1999 |

OTHER PUBLICATIONS

Schipper et al., Chitosans as Absorption Enhancers for Poorly Absorbable Drugs. 1: Influence of Molecular Weight and Degree of Acetylation on Drug Transport Across Human Intestinal Epithelial (Caco-2) Cells Pharm Res. Nov. 1996;13(11):1686-92.*
Richardson, Kolbe and Duncan, "Potential of low moecular mass chitosan as a DNA delivery system", Int. J. Pharmaceutics, vol. 178, pp. 231-242, 1999.
Erbacher et al., "Chitosan-based vector/DNA complexes for gene delivery", Pharmacetuical Research, vol. 15, pp. 1332-1339, 1998.
Hoggard et al., "Chitosan as a non-viarl gene delivery system", Gene Therapy, vol. 8, pp. 1108-1121, 2001.
Report and Recommendations of the Panel to Assess the NIH Investment in Research on Gene therapy, p. 11, Dec. 1995.
Goodman and Gilman's The Pharmacological Basis of Therapeutics, Ninth Edition, McGraw-Hill, pp. 77-101, 1996.
Marshall E. Gene Therapy's Growin Pains, Science, 25:1050, p. 1052-5, 1995.
Brown MD, Schatzlein AG, Uchegbu If. Gene delivery with synthetic (non viral) carriers, Int J. Parhm 229(1-2); 1-21, Oct. 23, 2001.
Mao et al., "Chitosan-DNA nanoparticles as gene carriers: synthesis, characterization and transfection efficiency" J. Control Release. 70(3): 399-421, Feb. 23, 2001.
Köping-Höggård et al., "Chitosan-pDNA Polyplex; In Vivo Gene Expression After Tracheal, Nasal and Oral Administration to Mice", Pharm. Sci., vol. 1 (suppl.), p. 5-278, 1998.
Köping-Höggård et al., "Chitosan-pDNA Polyplex: A New Efficient and Biodegradable Gene Delivery System in Vitro", Pharm. Sci., vol. 1 (suppl.), p. 5-285, 1998.
Lee, M. et al., "Water-soluble and low molecular weight chitosan-based plasmid DNA delivery", "Pharmaceutical Research", vol. 18, No. 4, pp. 427-431, 2001.
Koping-Hoggard, M. et al, "Chitosan as a vonviral gene delivery syste. Structure- property relationships and characteristics compared with polyethylenimine in vitro and after lung administration in vivo", Gene Therapy, vol. 8, 2001, pp. 1108-1121.
Richardson, Simon C.W., et al, "Potential of low molecular mass chitosan as a DNA delivery sytem: biocompatibility, body distribution and ability to complex and protect DNA", International Journal of Pharmaceutics, vol. 178, 1999, pp. 231-243.
Lee, Minhyung et al, "Water-soluble and low molecular weight chitosan-based plasmid DNA delivery", Pharmaceutical Research, vol. 18, No. 4, 2001, pp. 427-431.
Tommeraas, Kristoffer et al, "Preparation and characterisation of chitosans with oligosaccharide branches", Carbohydrate Research, vol. 337, 2002, pp. 2455-2462.
MacLaughlin et al., "Chitosan and depolymierzed chitosan oligomers as condensing carriers for in vivo plasmid delivery", J. Controlled Release, vol. 56, pp. 259-272, 1998.

* cited by examiner

Primary Examiner—Maria Leavitt

(57) ABSTRACT

The present invention concerns a composition comprising complexes of cationic chitosan oligomers derived from the cationic polysaccharide chitosan, wherein said cationic oligomers contain a weight fraction of less than 20% of oligomers with a Degree of Polymerization (DP)<10 in addition to a weight fraction of less than 20% with DP>50, and a nucleic acid. These compositions comprising well-defined cationic chitosan oligomers having a certain distribution of chain lengths, and nucleic acid are advantageous to achieve delivery of the nucleic acid into cells of a selected tissue, and to obtain in vivo expression of the desired molecules encoded for by the nucleic acid.

13 Claims, 14 Drawing Sheets

Figure 1:
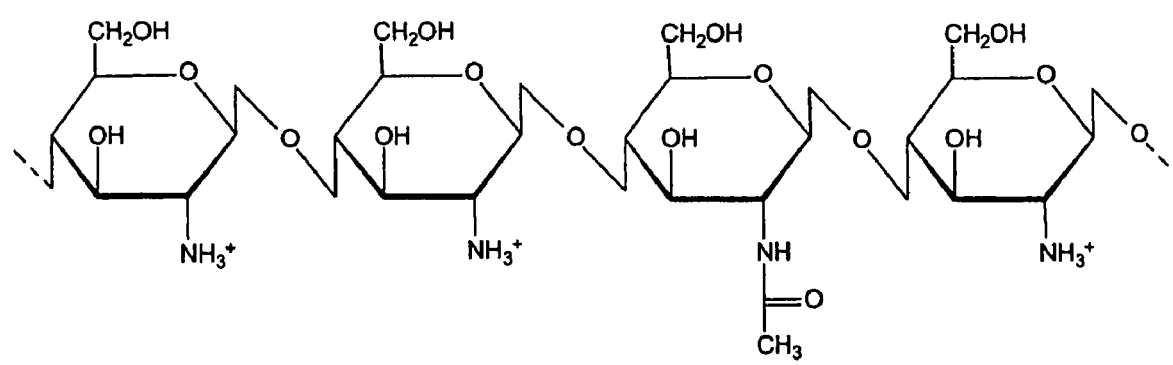

Acid hydrolysis: Primarily hydrolysis of N-acetyl-glucosamine residues
Enzymes: The linkages being hydrolysed depends on the type of enzyme
In both cases a new reducing end is formed

NON-VIRAL GENE DELIVERY SYSTEM

This application is a continuation of U.S. patent application Ser. No. 10/513,429 filed Nov. 3, 2004 (now abandoned), which is a national stage application (under 35 U.S.C. 371) of PCT/N003/00143 filed May 2, 2003, which claims the benefit of Norwegian application 2002 2148 filed May 3, 2002.

FIELD OF THE INVENTION

The present invention relates to a new non-viral delivery system for nucleic acids, and more specifically, to a system, which facilitates the introduction of nucleic acid into cells in a host tissue after administration to that tissue. This system is based on a composition comprising chemically and physical-chemically well-defined cationic chitosan oligomers derived from biodegradable chitosan polysaccharides that efficiently delivers biologically active nucleic acids, such as oligo or polynucleotides that encodes a desired product, and facilitates the expression of a desired product in cells present in that tissue.

BACKGROUND ART

The concept of gene therapy is based on that nucleic acids, DNA, RNA can be used as pharmaceutical products to cause in vivo production of therapeutic proteins at appropriate sites. Delivery systems for nucleic acids are often classified as viral and non-viral delivery systems. Because of their highly evolved and specialized components, viral systems are currently the most effective means of DNA delivery, achieving high efficiencies for both delivery and expression. However, there are safety concerns for viral delivery systems. The toxicity, immunogenicity, restricted targeting to specific cell types, limited DNA carrying capacity, production and packaging problems, recombination and a very high production cost hamper their clinical use (Luo and Saltzman, 2000). For these reasons, non-viral delivery systems have become increasingly desirable in both basic research laboratories and clinical settings. However, from a pharmaceutical point of view, the way of delivery of nucleic acids still remains a challenge since a relatively low expression is obtained in vivo with non-viral delivery systems as compared to viral delivery systems (Saeki et al., 1997).

A variety of non-viral delivery systems, including cationic lipids, peptides or polymers in complex with plasmid DNA (pDNA), have been described in the prior art (Boussif et al., 1995; Felgner et al., 1994; Hudde et al., 1999). The negatively charged nucleic acids interacts with the cationic molecules mainly through ion-ion interactions, and undergo a transition from a free form to a compacted state. In this state the cationic molecules may provide protection against nuclease degradation and may also give the nucleic acid-cationic molecule complex surface properties that favour their interaction with and uptake by the cells (Ledley, 1996).

Among these cationic molecules, the synthetic polymer polyethylenimine (PEI) have been shown to form stable complexes with pDNA and mediate relatively high expression of the transgene both in vitro and in vivo (Boussif et al., 1995; Ferrari et al., 1997; Gautam et al., 2001). For this reason, PEI is often used as a reference system in the experimental setup. However, a rough correlation between toxicity and efficiency has been suggested for PEI (Luo and Saltzman, 2000) and recent studies have addressed concerns about toxicity using PEI (Godbey et al., 2001; Putnam et al., 2001). Another drawback with PEI is that it is not biodegradable and it may therefore be stored in the body for a long time. Therefore, the search for effective and non-toxic biodegradable non-viral delivery systems is highly desirable.

Most commonly, non-viral delivery systems have been delivered in vivo by the parenteral route. After intravenous administration to mice, compacted nucleic acid-cationic molecule complexes deposited mainly in the lung capillaries where the gene was expressed in the endothelium of the capillaries in the alveolar septi (Li and Huang, 1997; Li et al., 2000; Song et al., 1997) or even in the alveolar cells (Bragonzi et al., 2000; Griesenbach et al., 1998), but not in the epithelium. However, unformulated, naked DNA was rapidly degraded in the blood circulation before it reached its target and generally resulted in no gene expression. In contrast, injection of naked DNA into skeletal muscle resulted in a dose-dependent gene expression (Wolff et al., 1990) which was further enhanced when complexed with a non-compacting but 'interactive' polymer such as polyvinyl pyrrolidone (PVP) or polyvinyl alcohol (PVA) (WO 9621470) (Mumper et al., 1996; Mumper et al., 1998). Thus, gene transfection in vivo is tissue-dependent in an unpredictable way and therefore remains a challenge.

Mucosal delivery of non-viral delivery systems has also been described that is delivery to the gastrointestinal tract, nose and respiratory tract (Koping-Hoggard et al., 2001; Roy et al., 1999), WO 01/41810. With exception for the delivery to the nasal tissue where DNA in uncompacted form gives the best gene expression (WO 01/41810) compacted nucleic acid-cationic molecule complexes are preferred to uncompacted DNA when a high gene expression is required in a mucosal tissue.

In prior art, non-viral gene delivery systems are based on cationic polymers such as chitosan of rather high molecular weight, often several hundred kilodaltons (kDa) with 5 kDa as a lower limit, see for example MacLaughlin et al., 1998, Roy et al., 1999 and WO 97/42975. The major reason is that polymers of lower molecular weight (<5 kDa) form unstable complexes with DNA, resulting in a low gene expression (Koping-Hoggard, 2001). However, there are many drawbacks using cations of high molecular weight such as increased aggregation of compacted nucleic acid-cationic molecule complexes and solubility problems (MacLaughlin et al., 1998). Further, there are several biological advantages of using cationic molecules of lower molecular weights that is they generally show reduced toxicity and reduced complement activation compared to cations of higher molecular weights (Fischer et al., 1999; Plank et al., 1999).

In the prior art some examples of the use of low molecular weight cations for complexation with nucleic acid have been described (Florea 2001; Godbey et al., 1999; Koping-Hoggard, 2001; MacLaughlin, et al., 1998; Sato et al., 2001). However, these low molecular weight cations form unstable compacts with DNA that separate in an electric field (agarose gel electrophoresis) resulting in no or a very low gene expression in vitro, as compared to cations of higher molecular weights. This can be explained by that complexes formed between DNA and low molecular weight cations are generally unstable and dissociate easily (Koping-Hoggard, 2001). In fact, the dissociation of cationic molecule-DNA compacts and release of naked DNA during agarose gel electrophoresis has often been used as an assay to distinguish ineffective formulations from effective ones in the literature (Fischer et al., 1999; Gebhart and Kabanov, 2001; Koping-Hoggard et al., 2001). Then, it is known from the prior art that complexes between DNA and cations should be stable to mediate a high gene expression.

The prior art contains various examples of methods for the delivery of nucleic acids to the respiratory tract using non-viral vectors (Deshpande et al., 1998; Ferrari et al., 1997; Gautam et al., 2000). We recently identified and characterized one such system based on the DNA-complexing polymer chitosan (Koping-Hoggard et al., 2001), a linear polysaccharide, which can be derived from chitin. Chitosan-based gene delivery systems are also described in U.S. Pat. No. 5,972,707 (Roy et al., 1999), WO 98/01160 and in US patent application no. 2001/0031497 (Rolland et al., 2001).

Chitosan has been introduced as a tight junction-modifying agent for improved drug delivery across epithelial barriers (Artursson et al., 1994). It is considered to be non-toxic after oral administration to humans and has been approved as a food additive and also incorporated into a wound-healing product (Illum, 1998).

Chitosans comprise a family of water-soluble, linear polysaccharides consisting of (1→4)-linked 2-acetamido-2-deoxy-β-D-glucose (GlcNAc, A-unit) and 2-amino-2-deoxy-β-D-glucose, (GlcN, D-unit) in varying composition and sequence (FIG. 1). The definition adopted here to distinguish between chitin and chitosan is based on the insolubility of chitin in dilute acid solution and the solubility of chitosan in the same dilute acid solution (Roberts, 1992).

The relative content of A- and D-units may be expressed as the fraction of A-units:

$F_A$=number of A-units/(number of A-units+number of D-units)

$F_A$ is related to the percentage of de-N-acetylated units through the relation:

% de-N-acetylated units=100%·(1−$F_A$)

Each D-unit contains a hydrophilic and protonizable amino group, whereas each A-unit contains a hydrophobic acetyl group. The relative amounts of the two monomers (that is A/D=$F_A$/(1−$F_A$)) can be varied over a wide range, and results in a broad variability in their chemical, physical and biological properties. This includes the properties of the chitosans in solution, in the gel state and in the solid state, as well as their interactions with other molecules, cells and other biological and non-biological matter.

The influence of the chemical structure of chitosans was recently demonstrated when chitosans were used in a non-viral gene delivery system (Koping-Hoggard et al., 2001). Chitosans of different chemical compositions displayed a structure dependent efficiency as gene delivery system. Only chitosans that formed stable complexes with pDNA gave a significant transgene expression. Such complexes required that at least 65% of the chitosan monomers were deacetylated.

Figure 2A:
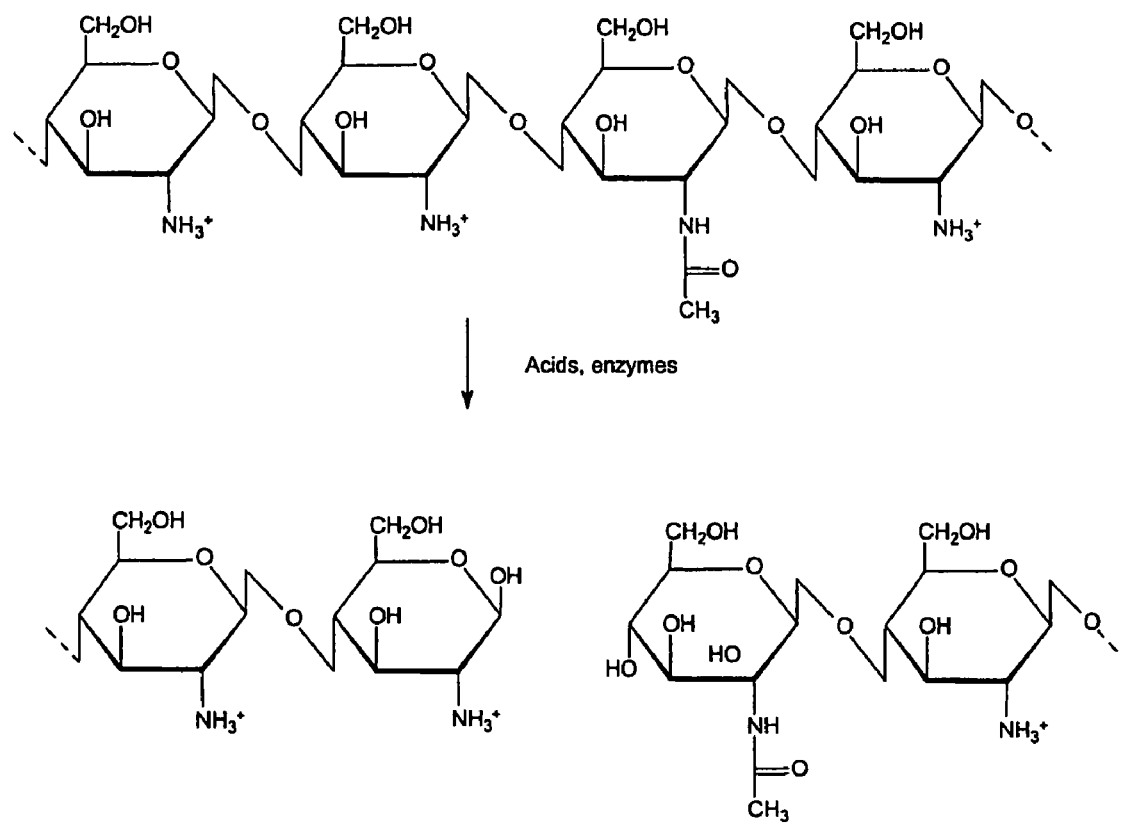
Figure 2B:
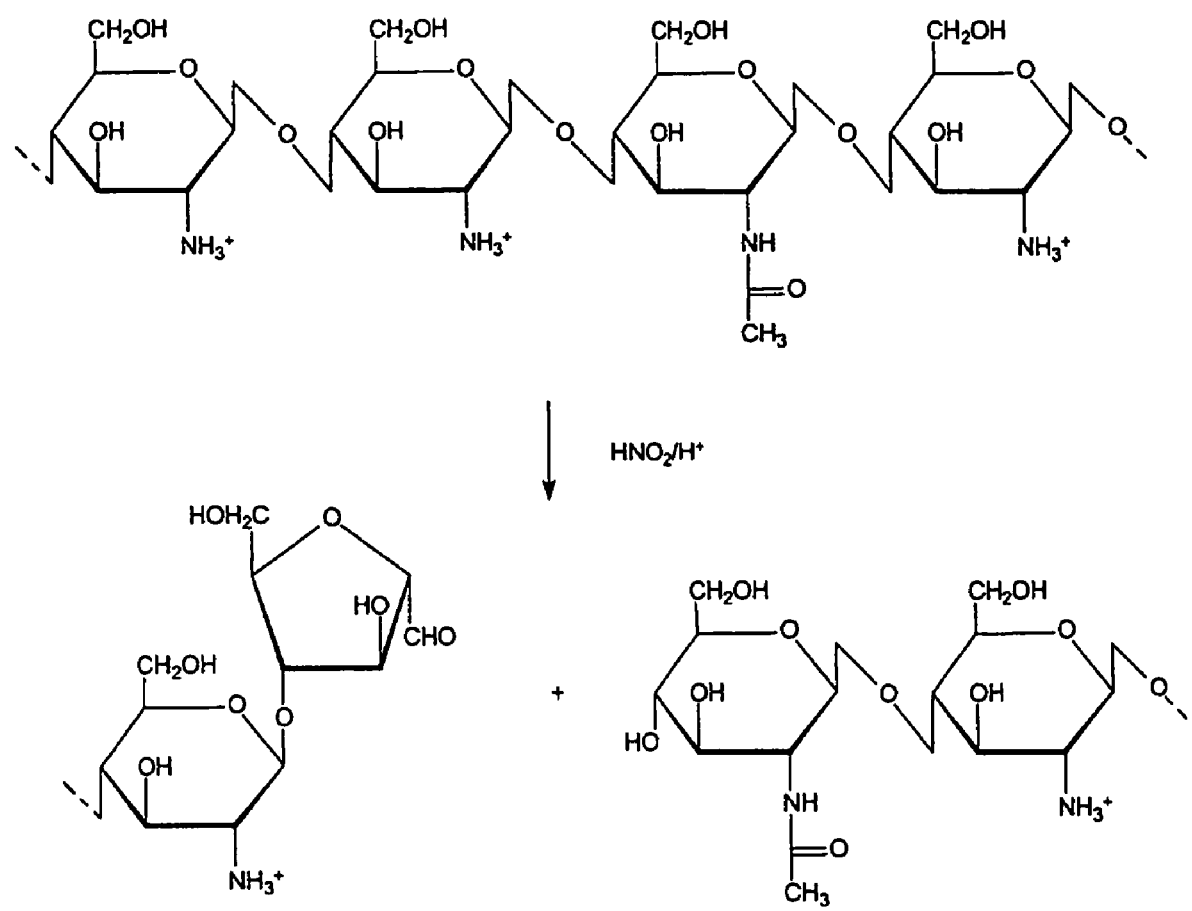

Chitosans can be depolymerized either chemically or enzymatically to obtain chitosan polymers or oligomers of the desired molecular size. Various chemical degradation mechanisms can be used to depolymerize chitosans, that is acid hydrolysis, nitrous acid and oxidative-reductive depolymerization. Ultrasonic depolymerisation of polymers may alternatively be used, but these methods are very inconvenient for producing very low molecular weights. Depolymerisation of chitosan by the use of nitrous acid is a convenient way of preparing low-molecular weight chitosan, as described in for example U.S. Pat. No. 3,922,260 and U.S. Pat. No. 5,312,908. This mechanism involves deamination of a D-unit, forming 2,5-anhydro-D-mannose unit at the new reducing end, which can be reduced to 2,5-anhydro-D-mannitol using NaBH$_4$ as shown in FIG. 2. Alternatively, various enzymes can also be used to depolymerize chitosan, for instance U.S. Pat. No. 5,482,843, chitosanases, chitinases, and lysozyme. Also acid hydrolysis may be used to depolymerise chitosan (Vårum et al., 2001, and references therein).

In the prior art, studies of the effect of molecular weight of chitosan on transfection efficiency in vitro of chitosan-pDNA complexes showed no significant dependence of the molecular weight in the size range 20-200 kDa (Koping-Hoggard et al., 2001; MacLaughlin et al., 1998). However, in another study (Sato et al., 2001) chitosans of 15 kDa and 52 kDa showed higher gene expression than chitosan>100 kDa, while no gene expression was detected with a 1.3 kDa chitosan. Further, studies of gene expression in vitro and in lung tissue in vivo using a series of low molecular weight chitosans (1.2 kDa, 2.4 kDa and 4.7 kDa) showed that only the 4.7 kDa chitosan mediated a significant gene expression (Koping-Hoggard, 2001).

Chitosans of different molecular weights have been used as components in complexes for non-viral gene delivery. For example, US patent application no. 2001/0031497A refers to the use of small molecular weight chitosan as a component of the delivery system, that is chitosan in the range of 2-4 kDa Mw, which resulted in the smallest particle of gene delivery system and also in an increased transfection of cells with the condensed delivery system in vitro.

Figure 3:
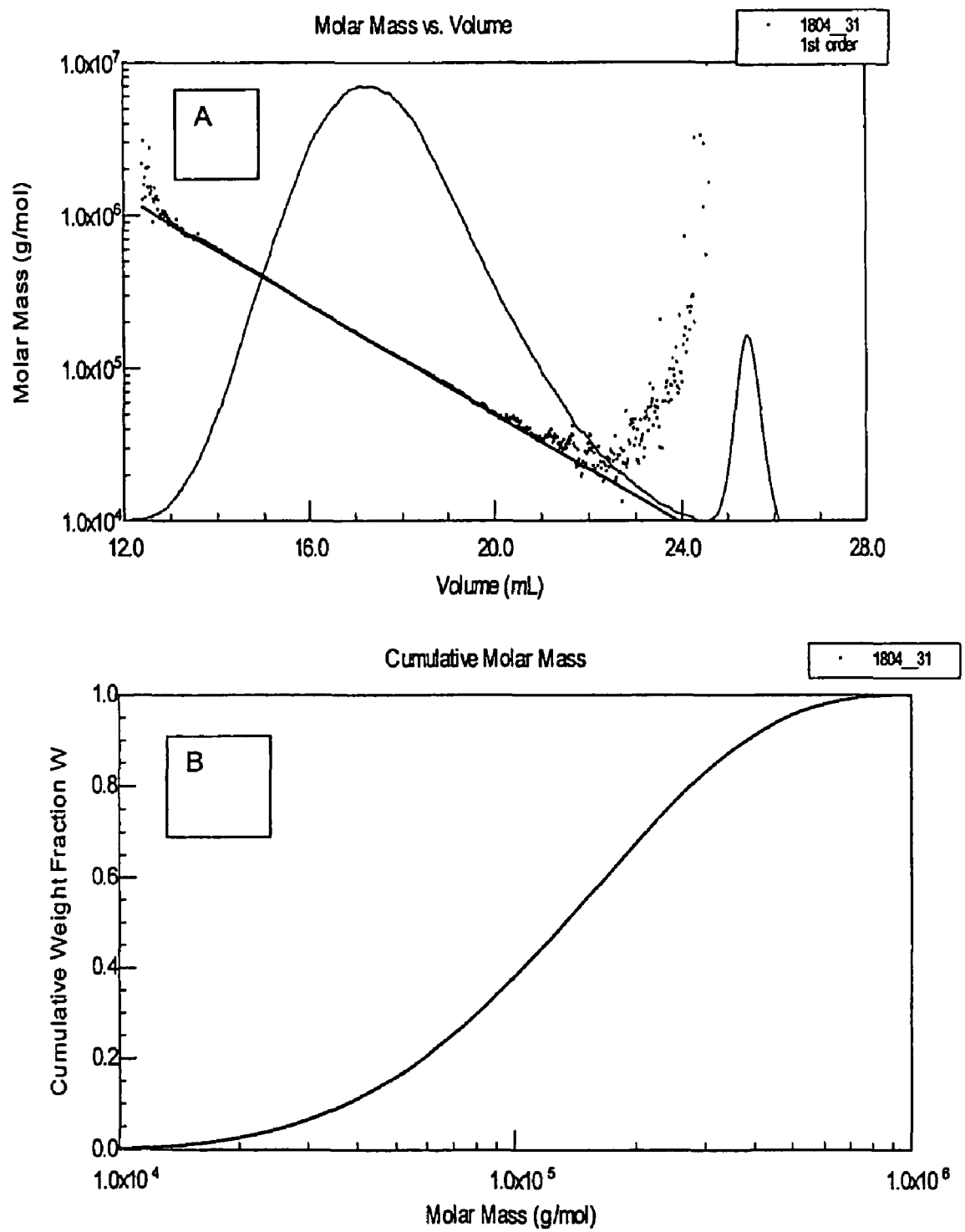

Chitosans of different molecular weights which are used in gene delivery systems are normally unfractionated samples obtained from commercial suppliers, and lower molecular weights are obtained from said samples by partial degradation using degradation agents such as organic or inorganic acids, nitric acid or chitosan degrading enzymes. In all cases, the distribution of molecular weights remains relatively high. As an example, a commercial chitosan with a weight average molecular weight ($M_w$) of 180.000 was analysed by size-exclusion chromatography using a refractive index detector and a multi-angle laser light scattering detector. FIG. 3A shows the elution profile, that is refractive index detector signal, which is proportional to the concentration of chitosan, combined with a plot of the calculated molecular weight (expressed as chitosan in the acetate salt form) as a function of the elution volume. It is evident that the sample contains molecular weights as high as $10^6$ g/mol (1000 kDa) at the beginning of the peak and as low as $10^4$ (10 kDa) at the end of the peak. A recalculation of these data gives the cumulative molecular weight distribution (FIG. 3B). It may be inferred from these calculations that 12% (w/w) of the sample has a molecular weight below 40 kDa and 38% of the sample has a molecular weight below 100 kDa. Likewise, 18% of the sample has a molecular weight above 300 kDa and 9% has a molecular weight above 400 kDa. The sample is thus polydisperse since it contains polymers of different molecular weights or chain lengths.

Chitosans may be supplied in the free amine form or as different salts such as chitosan chloride, chitosan glutamate and chitosan acetate. The salt-form influences the relationship between the molecular weight (M) and DP (the number of sugar residues per molecule). The following equations describe this relationship between DP and M:

Free base: M=DP (161(1−$F_A$)+203$F_A$)=DP (161+42$F_A$)

Chitosan chloride: M=DP (197.45(1−$F_A$)+203$F_A$)=DP (197.45+5.55$F_A$)

Chitosan acetate: M=DP (221(1−$F_A$)+203$F_A$)=DP (221−18$F_A$)

Chitosan glutamate: M=DP (308(1−$F_A$)+203$F_A$)=DP (308−105$F_A$)

The weight average molecular weight ($M_w$) of a polydisperse sample may be expressed as $M_w=\Sigma c_i M_i/\Sigma c_i$ where $c_i$ is the concentration (g/l) of a particular molecular weight ($M_i$) within the distribution) (Tanford, C. (1961) Physical chemistry of macromolecules, John Wiley and Sons, New York, Section 8b). Likewise, the number average molecular weight ($M_n$) may be expressed as $M_n=\Sigma c_i/\Sigma(c_i/M_i)$. In the case referred to above $M_w$=180 kDa and $M_n$=84.5 kDa, and the polydispersity index which is defined as $M_w/M_n$ equals 2.1. A polydispersity near 2 is characteristic of a linear polymer which has been subjected to random depolymerisation (Tanford, C. (1961) Physical chemistry of macromolecules, John Wiley and Sons, New York, Section 33a)

The distribution of chain lengths following a random depolymerisation of a linear polymer such as chitosan is given by the equation (Tanford (1961):

$$W_x = xp^{x-1}(1-p)^2$$

$W_x$ is the weight fraction of chains containing x monomers (for chitosan the monomers are sugar residues) and p is the fraction of intact linkages and 1–p is the fraction of cleaved linkages. The number average degree of polymerisation ($x_n$) equals 1/(1–p). Since $M_n=M_0 x_n$, where $M_0$ is the monomer equivalent weight, which is 203 g/mol for a residue of N-acetyl-glucosamine when it occurs within a chitosan chain and 161 g/mol for a residue of glucosamine in the free base form when it occurs within a chitosan chain. For a given $F_A$ the average $M_0$ becomes equal to $203 \cdot F_A + 161 \cdot (1-F_A)$.

Figure 4:
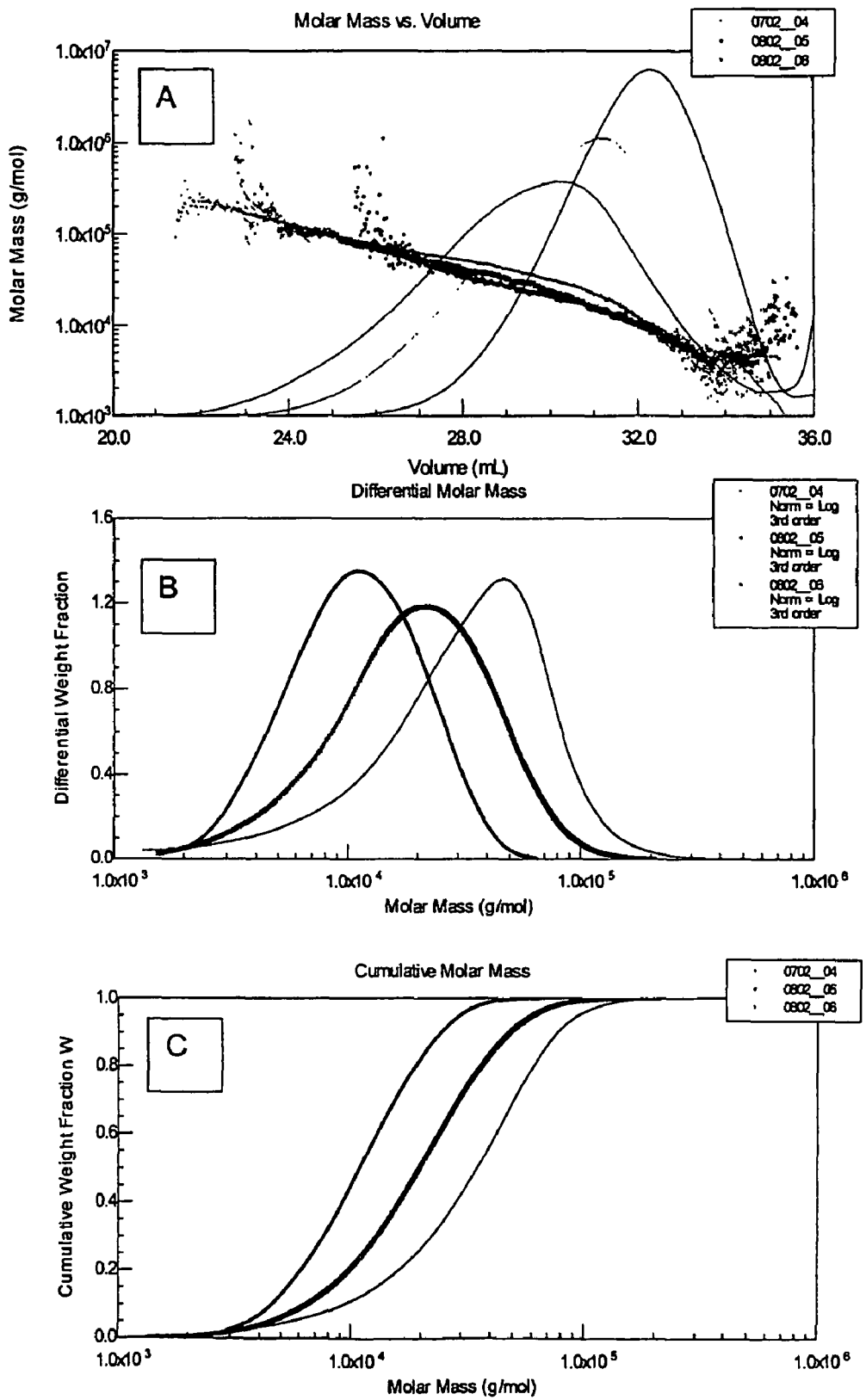

FIG. 4 shows SEC-MALLS chromatograms (4A), and differential (4B) and cumulative (4C) molecular weight distributions of a chitosan, which has been depolymerised by nitrous acid to obtain different weight average molecular weights in the range from 41.500 to 13.400. It is clearly shown that the calculated molecular weight distributions remain broad. These data clearly demonstrate that chitosans of different molecular weights which are produced from a high molecular weight by partial degradation remain polydiserse and contain chains of widely differing molecular weights.

The molecular weight distribution of a polymer may be modified by selectively removing certain parts of the distribution. Chitosan samples with relatively short chains may be fractionated by gel filtration to obtain individual oligomers or fractions with relatively narrow molecular weight distributions. One example is given by Tøommeraas et al. (2001) who obtained purified chitosan oligomers in the range of 2-10 residues per chain.

Samples with higher molecular weights may also be fractionated by gel filtration as demonstrated for chitosans by Ottøy et al. (1996). Typically, fractions with $M_w/M_n$ values of 1.2-1.5 was obtained by fractionating a normally polydisperse sample with $M_w$=270.000 using a gel filtration column containing Sepharose CL-4B and Sepharose CL-6B.

In an alternative method polydisperse chitosans may be fractionated by dialysis or membrane techniques which allow selective removal of the shortest chains, and where the resulting distribution depends on the initial distribution as well as the membrane characteristics porosity and transport coefficients and the operating conditions.

According to the present invention it was surprisingly discovered that chitosans of a single chain length or chitosans with narrow molecular weight distributions had different properties as complexing agents in gene delivery than other samples of comparable $M_w$ or $M_n$, but with broader molecular weight distributions.

Another disadvantage of many cations used for complexation of nucleic acid e.g. PEI, polylysine and chitosan is that they are roughly processed bulk chemicals with a broad molecular weight distribution and hence rather undefined (Godbey et al., 1999). It is well established that such chemicals may display a batch to batch variation. Therefore, from a pharmaceutical point of view, well-defined polycations having a narrow molecular weight distribution are preferred.

Another disadvantage using broad molecular weight polycations for complexation of nucleic acids and subsequent transfection is that chains of differents lengths may have different complexation and transfection effectivities.

SUMMARY OF THE INVENTION

The present invention is concerned with a composition comprising complexes of:
(a) cationic chitosan oligomers derived from the cationic polysaccharide chitosan wherein said cationic oligomers contain a weight fraction of less than 20% of oligomers with a Degree of Polymerization (DP)<10 in addition to a weight fraction of less than 20% with DP>50; and
(b) a nucleic acid.

According to the present invention it has unexpectedly been found that compositions comprising well-defined cationic chitosan oligomers having a certain distribution of chain lengths, and nucleic acid are advantageous to achieve delivery of the nucleic acid into cells of a selected tissue and to obtain in vivo expression of the desired molecules encoded for by the nucleic acid.

It is another object of the invention to provide a method of preparing compositions according to the invention, comprising the steps of:
(a) exposing said cationic chitosan oligomers to an aqueous solvent,
(b) mixing the aqueous solution of step (a) with said nucleic acid in an aqueous solvent, and
(c) reduce the volume of the product solution obtained in step (b) to achieve a desired concentration of the said composition.

It is yet another object of the present invention to provide a method of administering a nucleic acid to a mammal, by introduction of the composition, of the invention, into the mammal.

A further object of the present invention are the use of the composition of the invention in the manufacture of a medicament for prophylactic or therapeutic treatment of a mammal, or in the manufacture of a diagnostic agent for the use in in vitro or in vivo diagnostic methods.

These and other objects of the invention are provided by one or more of the embodiments described below.

DETAILED DESCRIPTION OF THE INVENTION

The composition according to the present invention can be derived from cationic polysaccharide chitosan by the use of chemical or enzymatic methods.

A preferred composition of the invention is wherein said cationic oligomers contain preferably a weight fraction of less than 20% of oligomers with DP<12 in addition to a weight fraction of less than 20% with a DP>40 and most preferably a weight fraction of less than 20% of oligomers with DP<15 in addition to a weight fraction of less than 20% with a DP>30.

Compositions comprising complexes between low molecular weight cationic chitosan oligomers and nucleic acid are described, wherein the cationic chitosan oligomers have well-defined chain lengths, narrow distribution of chain lengths and a well-defined chemical composition. Typically, the cationic chitosan oligomer has a molecular weight between 500 and 10,000 Da, preferably between 1,200 and 5,000 Da and most preferably between 3,000 and 4,700 Da. Typically the cationic chitosan oligomer has a fraction of A-units ($F_A$) of 0-0.35 (65-100% de-N-acetylated units), preferably between 0-0.1 (90-100% de-N-acetylated units) and most preferably between 0-0.01 (99-100% de-N-acetylated units). Suitably, said nucleic acid comprises a coding sequence that will express its function when said nucleic acid is introduced into a host cell.

According to one embodiment of the invention, said oligomers are derived from cationic polysaccharide chitosans followed by fractionating a polydisperse oligomer pool into oligomers having well-defined chain lengths, narrow distribution of chain lengths and a fraction of A-units ($F_A$) of 0-0.35 (65-100% de-N-acetylated units), preferably between 0-0.1 (90-100% de-N-acetylated units) and most preferably between 0-0.01 (99-100% de-N-acetylated units). Typically, said oligomers consist of 6-50 monomer units, preferably of 10-30 monomer units and most preferably of 15-25 monomer units, having a molecular weight between 3,000 and 4,700 Da, and a $F_A$ of less than 0.01 (more than 99% de-N-acetylated units).

According to another embodiment of the composition of the invention, said nucleic acid is selected from the group consisting of RNA and DNA molecules. These RNA and DNA molecules can be comprised of circular molecules, linear molecules or a mixture of both. Preferably, said nucleic acid is comprised of plasmid DNA.

According to a preferred embodiment of the present invention, said nucleic acid comprises a coding sequence that will express its function when said nucleic acid is introduced into a host cell. For instance it can encode a biologically active product, such as a protein, polypeptide or a peptide having therapeutic, diagnostic, immunogenic, or antigenic activity.

The present invention is also concerned with compositions as described above wherein said nucleic acid comprises a coding sequence encoding a protein, an enzyme, a polypeptide antigen or a polypeptide hormone or wherein said nucleic acid comprises a nucleotide sequence that functions as an antisense molecule, such as RNA.

Preferably the composition of the invention has a pH range between 3.5 and 8.

The composition of the invention can also preferably be derivatized with targeting ligands and/or stabilizing agents.

A further aspect of the invention is related to the liquid droplet size of said composition after nebulization. Preferably, the droplet size of the composition of the invention is essentially equal to the droplet size of naked pDNA after nebulization.

The present invention is also directed to a method for preparing the present composition, said method comprising the steps of: providing the present cationic chitosan oligomer as described above, (a) exposing said cationic chitosan oligomers to an aqueous solvent in the pH range 3.5-8.0, (b) mixing the aqueous solution of step (a) with said nucleic acid in an aqueous solvent and (c) dehydrating the product solution obtained in step (b) to achieve a high concentration of the composition before administration in vivo. Step (c) can be obtained by (1) evaporating the liquid of the product solution in step (b) to obtain the desired concentration, or (2) lyophilize the product solution in step (b) followed by reconstitution of the lyophilizate to obtain the desired concentration of the composition. Typically, said nucleic acid is present at a concentration of 1 ng/ml-300 μg/ml, preferably 1 μg/ml-100 μg/ml and most preferably 10-50 μg/ml in step (b) and 10 ng/ml-3,000 μg/ml, preferably 10 μg/ml-1,000 μg/ml and most preferably 100-500 μg/ml in step (c) using the evaporating method (1).

It should be understood, that a person skilled in the art can form the present composition at different amine/phosphate charge ratios to include negative, neutral or positive charge ratios. However a preferred embodiment is wherein the composition of the invention has a net positive charge.

The present invention is further concerned with a method of administering nucleic acid to a mammal, using the composition of the present invention, and introducing the composition into the mammal. Preferably, said composition is introduced into the mammal by administration to mucosal tissues by pulmonary, nasal, oral, buccal, sublingual, rectal, or vaginal routes. According to another preferred embodiment, said composition is introduced into the mammal by parenteral administration such as intravenous, intramuscular, intradermal, subcutaneous or intracardiac administration.

The present invention is also concerned with use of the composition of the invention in the manufacture of a medicament for prophylactic or therapeutic treatment of a mammal, or in the manufacture of a diagnostic agent for the use in in vivo or in vitro diagnostic methods, and specifically in the manufacture of a medicament for use in gene therapy, antisense therapy or genetic vaccination for prophylactic or therapeutic treatment of malignancies, autoimmune diseases, inherited disorders, pathogenic infections and other pathological diseases.

Other objects, features and advantages of the present invention will become apparent from the following detailed description. It should be understood, however, that the detailed description and specific examples, while indicating preferred embodiments of the invention, are given by the way of illustration only, since various changes and modifications within the spirit and scope of the invention will become apparent to those skilled in the art from this detailed description.

DESCRIPTION OF THE DRAWINGS

FIG. 1 shows the chemical composition of chitosan, where a fragment of the chitosan chain contains one residue of N-acetyl-β-D-glucosamine (A-unit) and 3 residues of β-D-glucosamine (D-units). The amino group of the D-units may be on a protonated or unprotonated form depending on pH.

FIG. 2*a* shows the chemical structure which is obtained after depolymerisation of a chitosan by acid or by a chitosanase. Acids cleave preferentially the glycosidic bond following an A-unit (A-unit at the newly formed reducing end). Enzymes vary in their specificities by hydrolysing both kinds of residues.

FIG. 2B shows the depolymerisation of chitosan by nitric acid, which only attacks D-residues, which are rearranged to form 2,5-anhydro-D-mannose.

FIG. 3 shows results where a commercial chitosan with a weight average molecular weight ($M_w$) of 180.000 was analysed by size-exclusion chromatography using a refractive index detector and a multi-angle laser light scattering detector. Columns: TSK G6000PWXL, 5000PWXL and 4000 PWXL (serially connected). Eluent: 0.2 M ammonium acetate, pH 4.5. RI detector: Optomed DSP (Wyatt). Light scattering detector: DAWN DSP (Wyatt). Processing parameters (Astra software v. 4.70.07): dn/dc=0.142 ml/g (determined off-line for chitosan acetate, the value was found to be independent of $F_A$). $A_2$: $5.0 \cdot 10^{-3}$ $mol \cdot ml \cdot g^{-2}$.

3A: Elution profile, that is refractive index detector signal, which is proportional to the concentration of chitosan, combined with a plot of the calculated molecular weight in this case expressed as chitosan in the acetate salt form as a function of the elution volume.

3B: The cumulative molecular weight distribution calculated from the data given in 3A.

FIG. 4 shows SEC-MALLS chromatograms (4A), and differential (4B) and cumulative (4C) molecular weight distributions of a chitosan, which has been depolymerised by nitrous acid to obtain different weight average molecular weights in the range from 41.500 to 13.400. Experimental conditions were the same as in FIG. 3.

Figure 5:
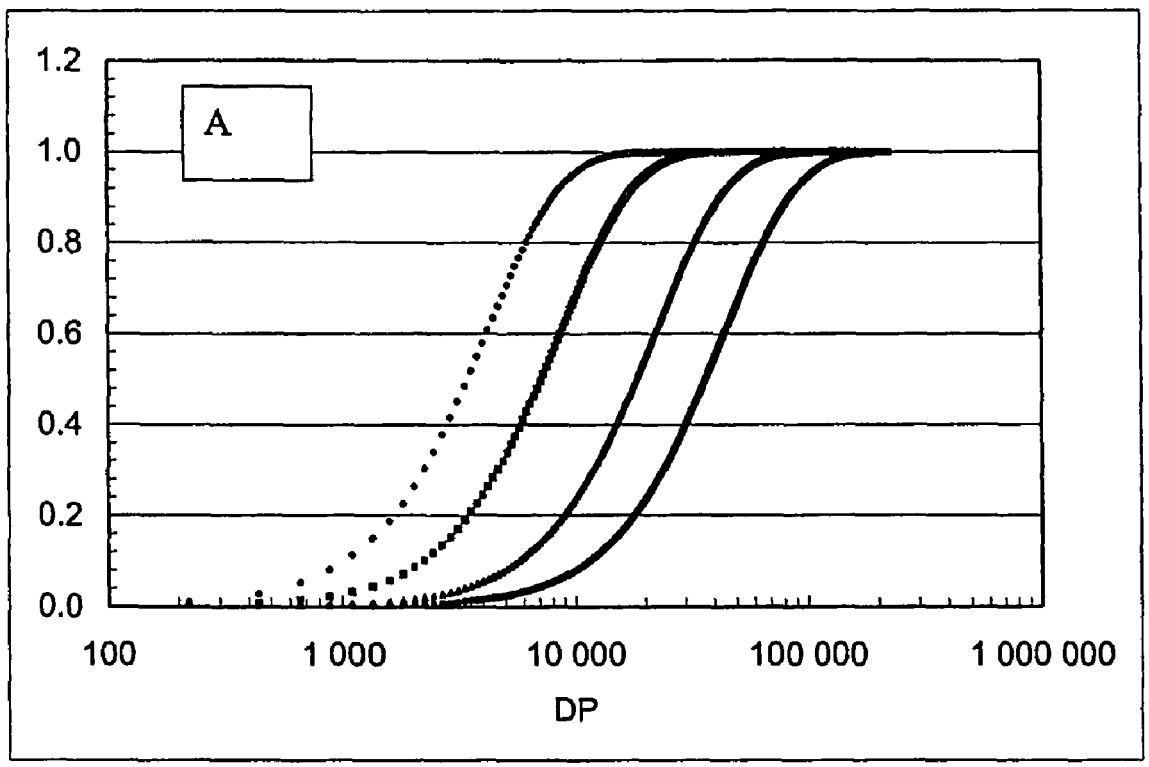
Figure 5:
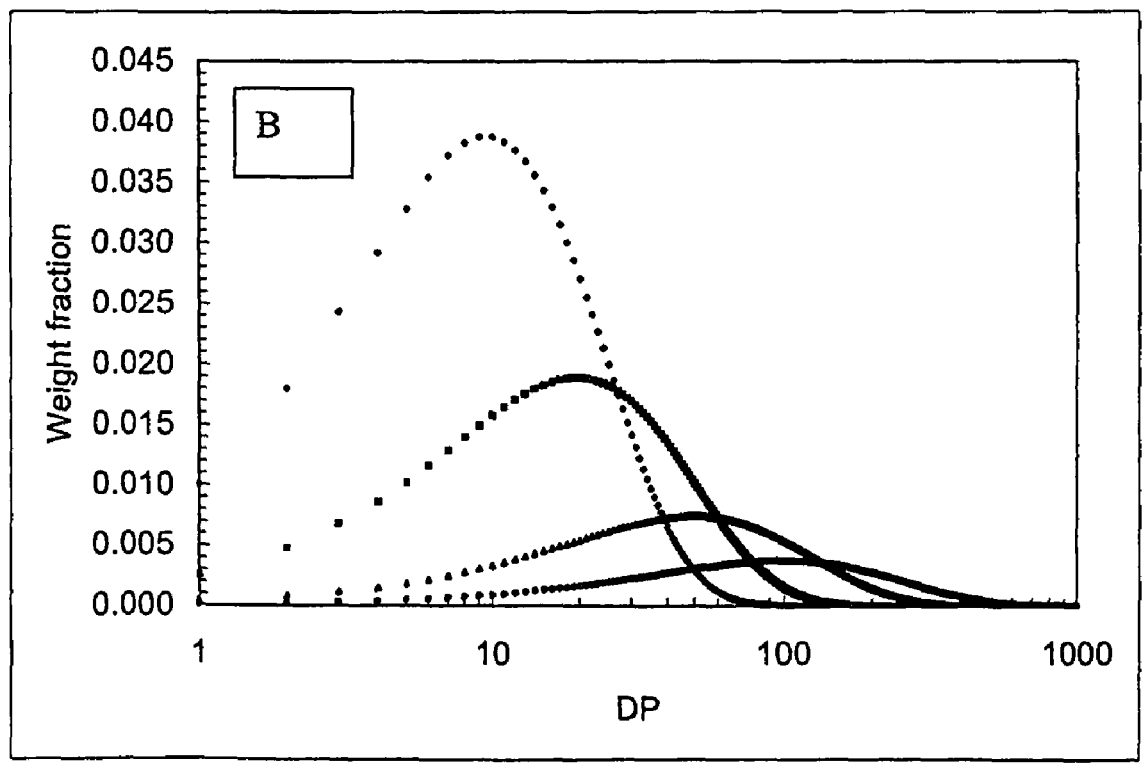

FIG. 5: Calculated cumulative (A) and differential (B) molecular weight distributions corresponding to the Kuhn distribution for chitosan depolymerised to obtain 100, 50, 20 and 10 residues ($DP_n$).

Figure 6:
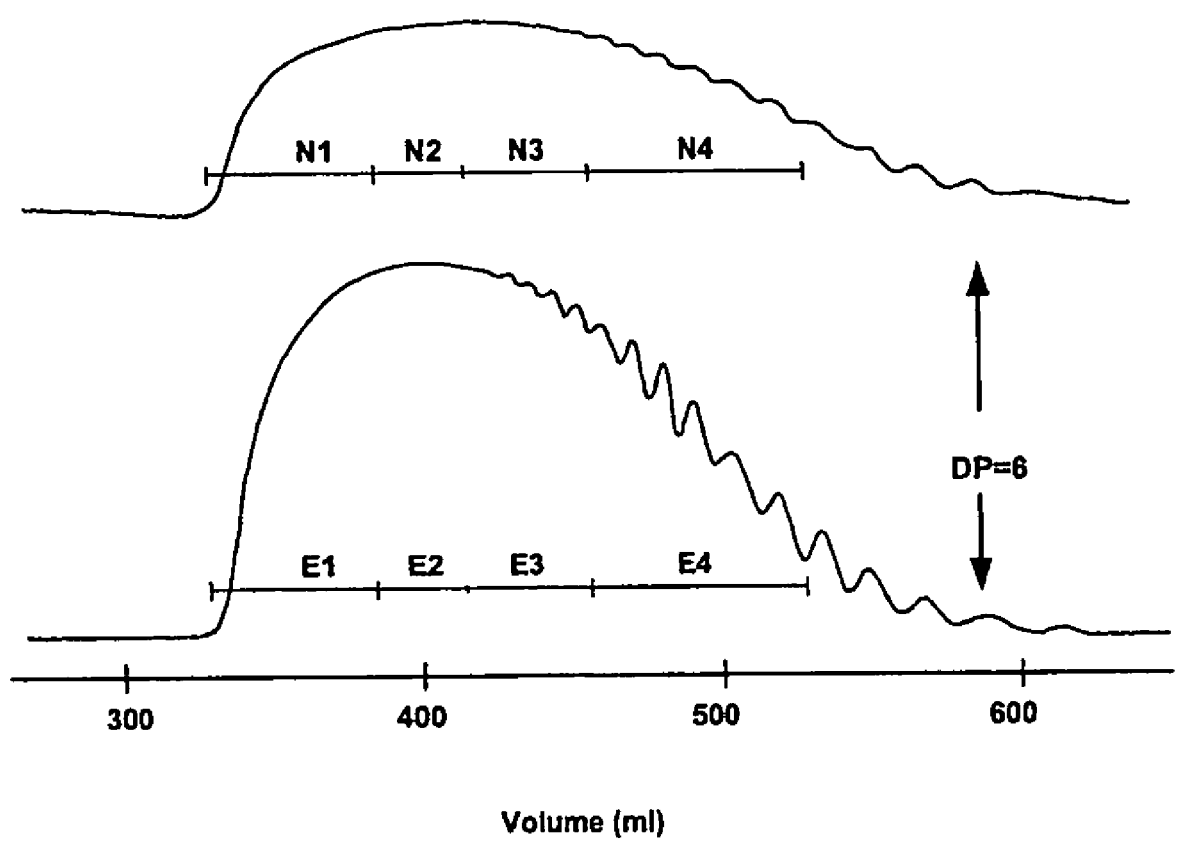

FIG. 6: Size-exclusion chromatograms of a fully de-N-acetylated chitosan ($F_A<0.001$) which has been depolymerized by a) nitrous acid and reduced with $NaBH_4$ (N1-N4) or b) chitosanase (E1-E4) (Superdex 30; two 2.5×100 cm columns in series, eluent: 0.15M ammonium acetate, pH 4.5, flow rate 0.8 m/min). DP=6 indicates the elution volume of a fully de-N-acetylated chitosan hexamer.

Figure 7:
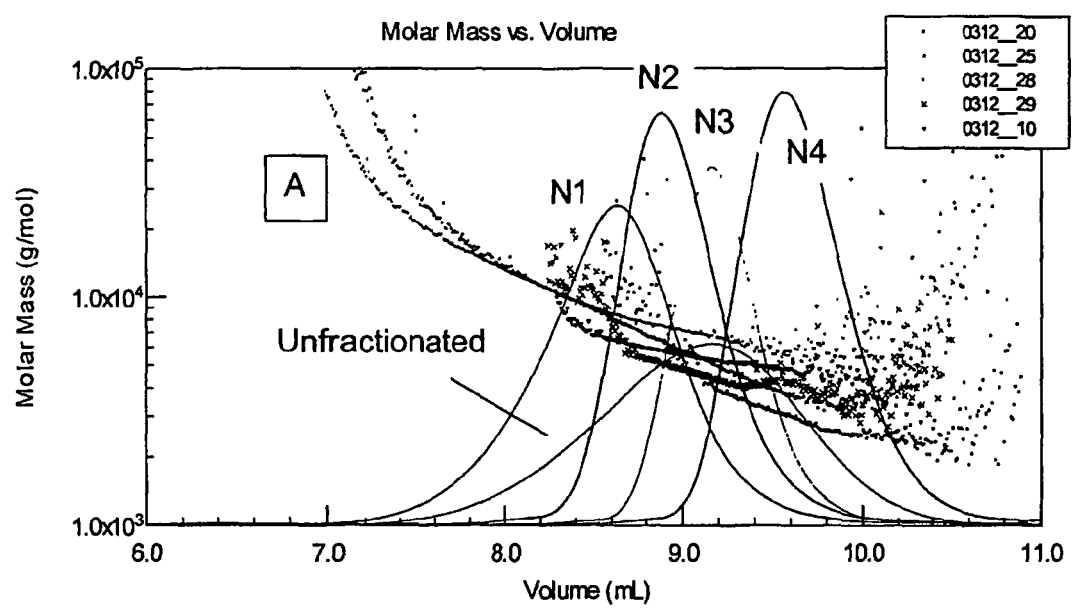
Figure 7:
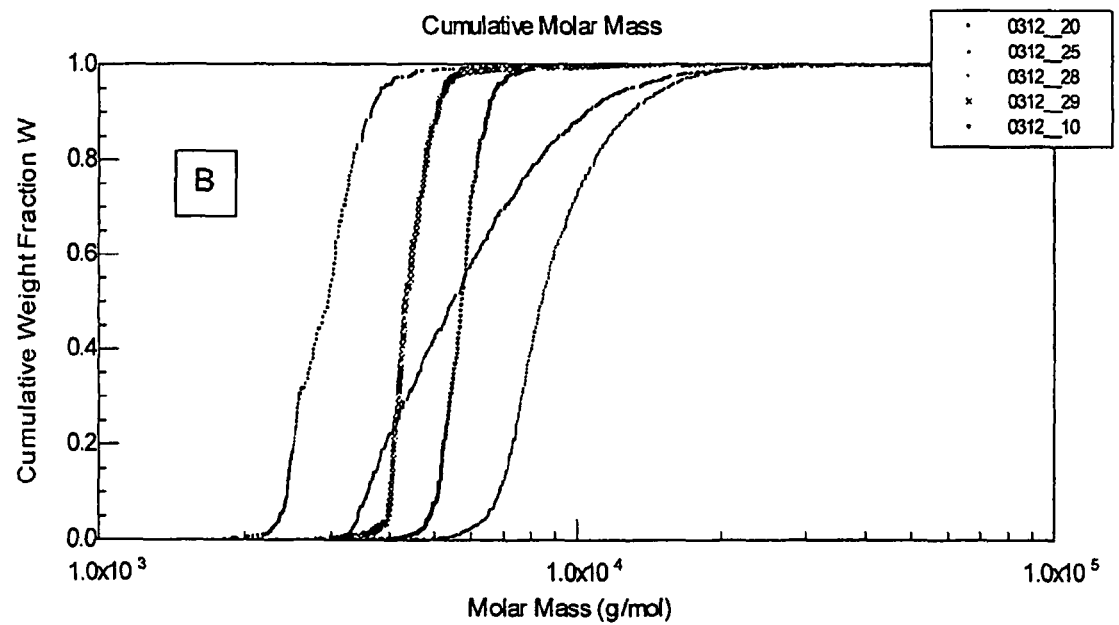

FIG. 7: SEC-MALLS chromatograms (7A) of a fully de-N-acetylated chitosan ($F_A<0.001$), which has been depolymerised by nitrous acid and reduced with $NaBH_4$ (un-fractionated sample) and fractions N1-N4 obtained as described in FIG. 6. The experimental conditions were the same as in FIG. 3 except that a single column (TSK G3000 PWXL) was used. FIG. 7B shows the corresponding cumulative molecular weight distributions calculated from the data given in 7A.

Figure 8:
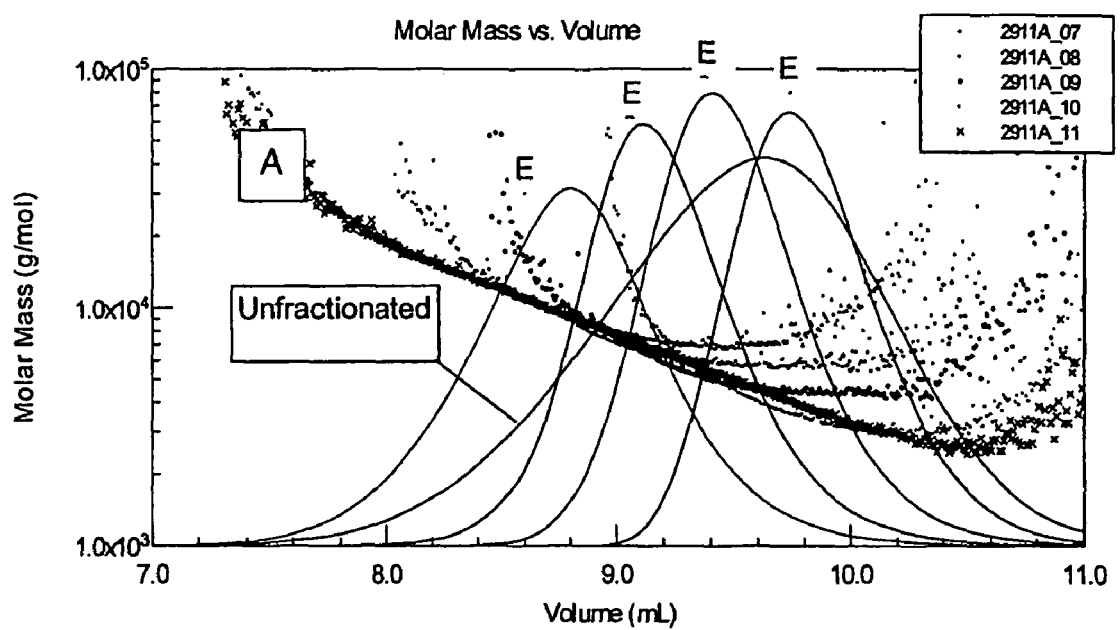
Figure 8:
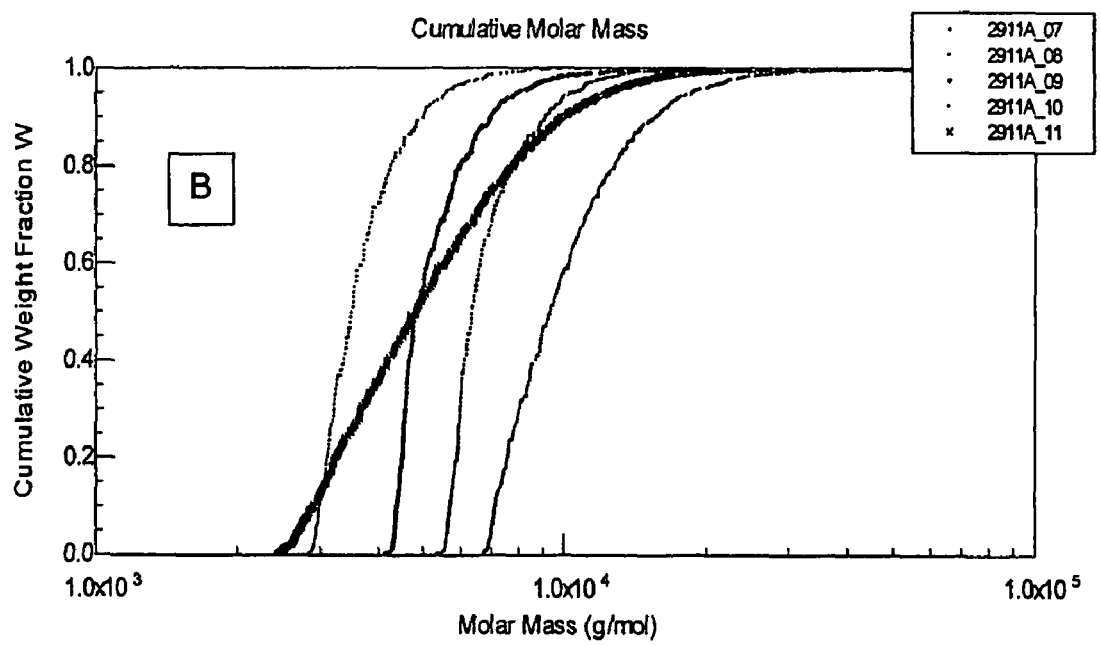

FIG. 8: SEC-MALLS chromatograms (8A) of a chitosan, which has been depolymerised by a chitosanase (un-fractionated sample) and fractions E1-E4 obtained as described in FIG. 6. The experimental conditions were the same as in FIG. 3 except that a single column (TSK G3000 PWXL) was used. FIG. 8B shows the corresponding cumulative molecular weight distributions calculated from the data given in 7A.

Figure 9:
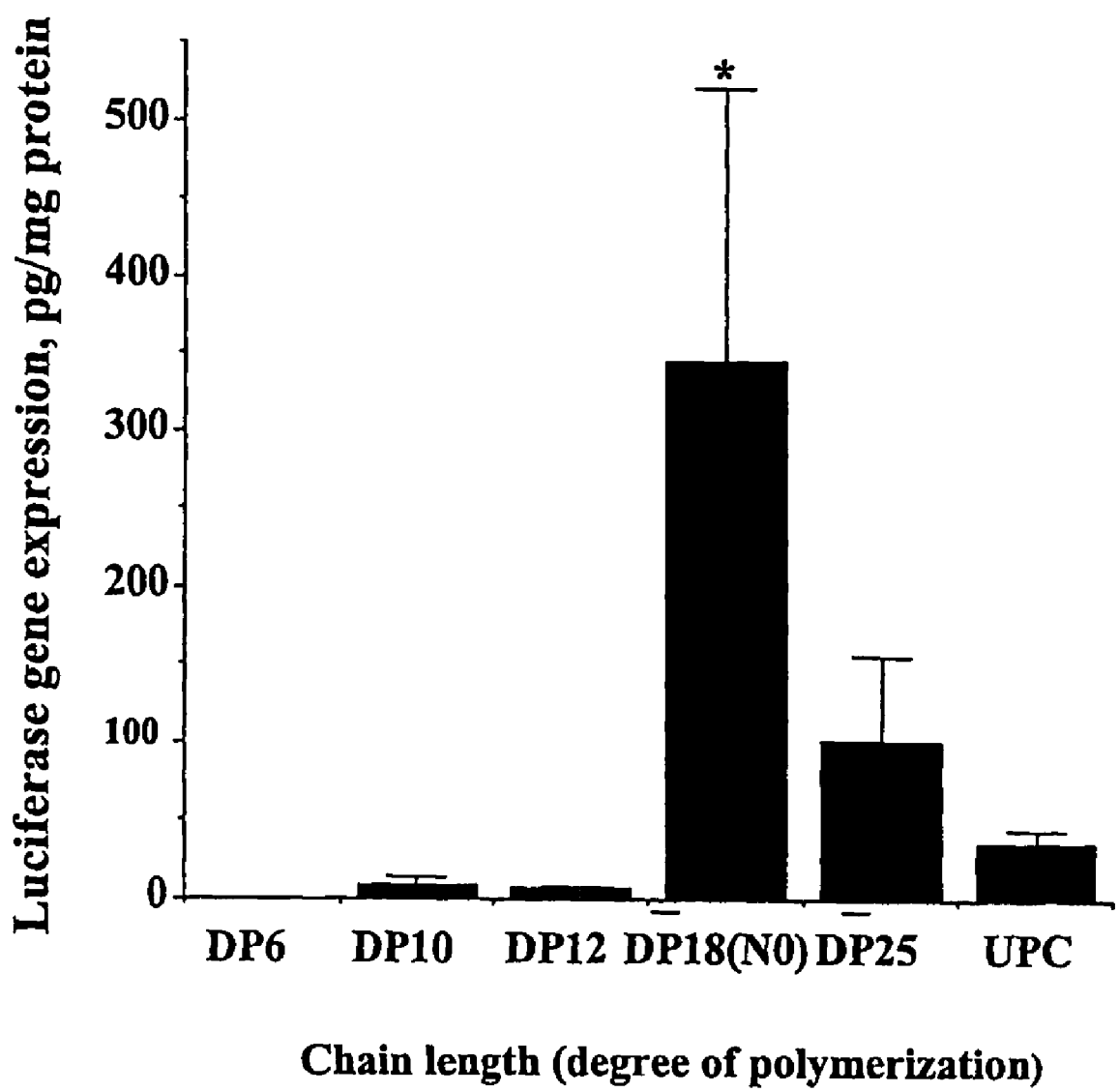

FIG. 9 shows in vivo lung luciferase expression (pg/mg) 3 days after intra-tracheal administration of 25 μg pLuc in mice (four animals per group). Complexes between chitosan oligomers and pLuc were prepared at an amine/phosphate charge ratio of 60:1 (+/−). The significantly highest luciferase expression was obtained with pLuc complexed with the chitosan oligomer N0 having 18 as the number average degree of polymerisation, as determined by $^{13}C$-NMR-spectroscopy. Statistical differences between mean values were investigated using ANOVA. Differences between group means were considered significant at P<0.05.

Figure 10:
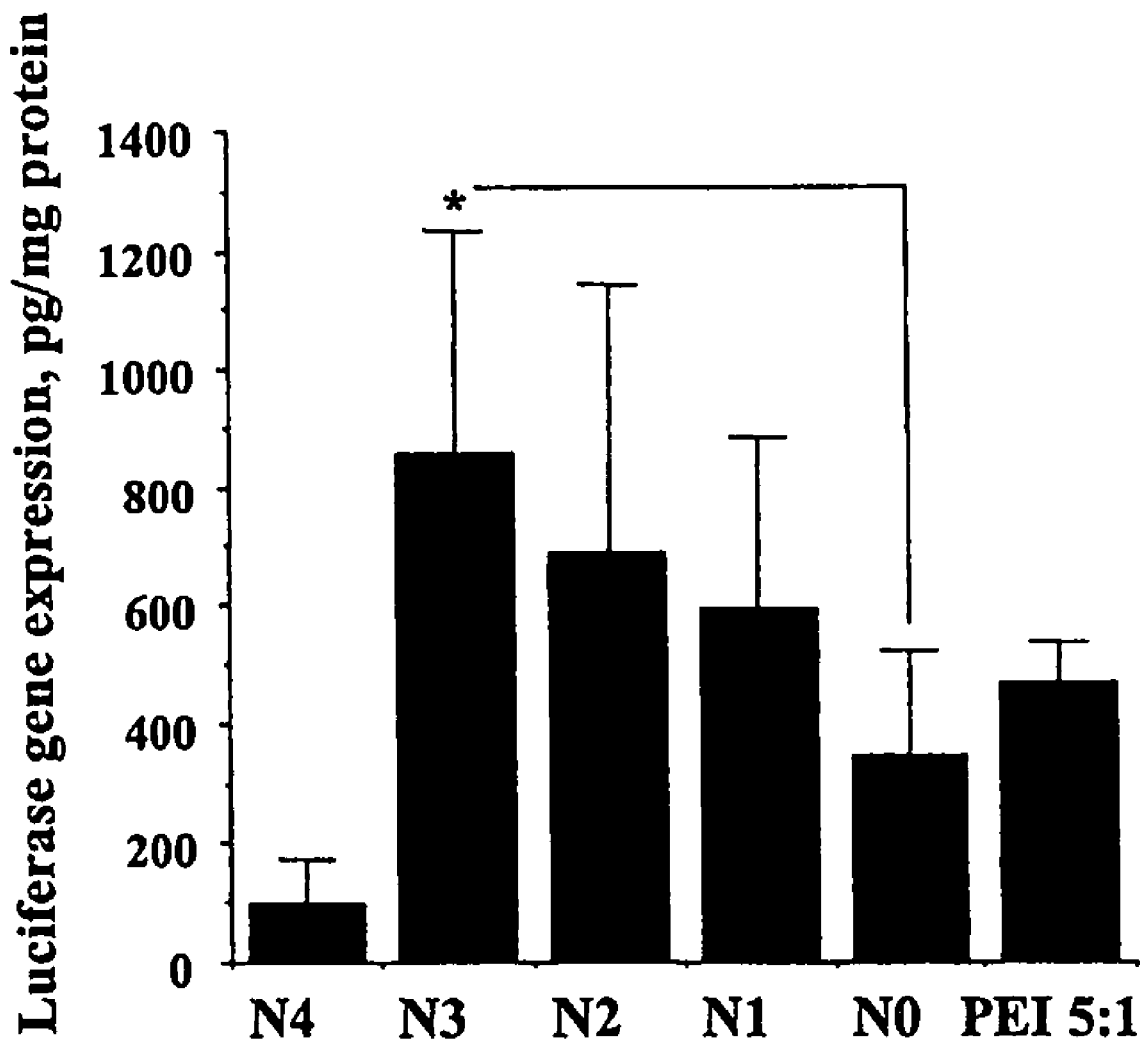

FIG. 10 shows in vivo lung luciferase expression (pg/mg) 3 days after intra-tracheal administration of 25 μg pLuc in mice (four animals per group). The chitosan oligomer N0 having 18 as the number average degree of polymerization was fractionated into four different samples having well-defined and narrow distributions of their degrees of polymerization. Complexes between chitosan oligomers and pLuc were prepared at an amine/phosphate charge ratio of 60:1 (+/−). Complexes based on the fraction containing oligomers having chain lengths between 15-21 monomer units (N3), showed significantly (p<0.05) higher gene expression compared to complexes based on the unfractionated sample N0 having 18 as the number average degree of polymerization. Statistical differences between mean values were investigated using ANOVA. Differences between group means were considered significant at P<0.05.

Figure 11:

FIG. 11 shows results of the agarose gel retardation assay. Complexes between chitosan oligomers and pLuc were prepared at an amine/phosphate charge ratio of 60:1 (+/−). With increasing molecular weight (degree of polymerization) of the chitosan oligomer, a higher stability of formed complexes was observed. Thus, complete retention of pLuc was detected with complexes formed with the fraction containing 36-50 monomer units (N1) as compared to complexes formed with 15-21 monomer units (N3).

Figure 12:
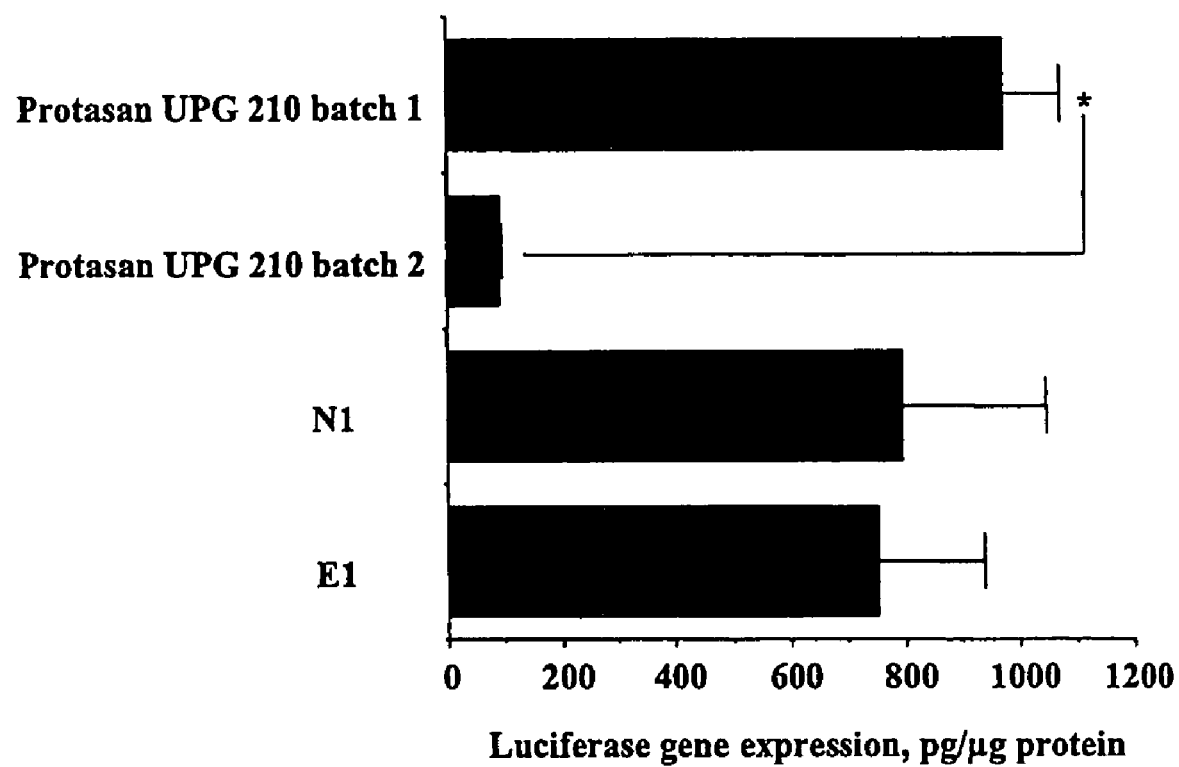

FIG. 12 shows the luciferase gene expression in vitro after incubating 293 cells with two batches of fractionated low molecular weight cationic chitosan oligomers (N1 and E1) prepared 9 months apart and commercial chitosan (Protasan UPG 210) ordered 3 years apart, respectively. The gene expression varied 10-fold between the two batches of Protasan UPG 210 complexed with pLuc at an amine/phosphate charge ratio of 2.4:1 (+/−) but not significantly between the two batches of fractionated low molecular weight cationic chitosan oligomers (N1 and E1) complexed with pLuc at an amine/phosphate charge ratio of 10:1 (+/−). Statistical differences between mean values were investigated using ANOVA. Differences between group means were considered significant at P<0.05.

Figure 13:
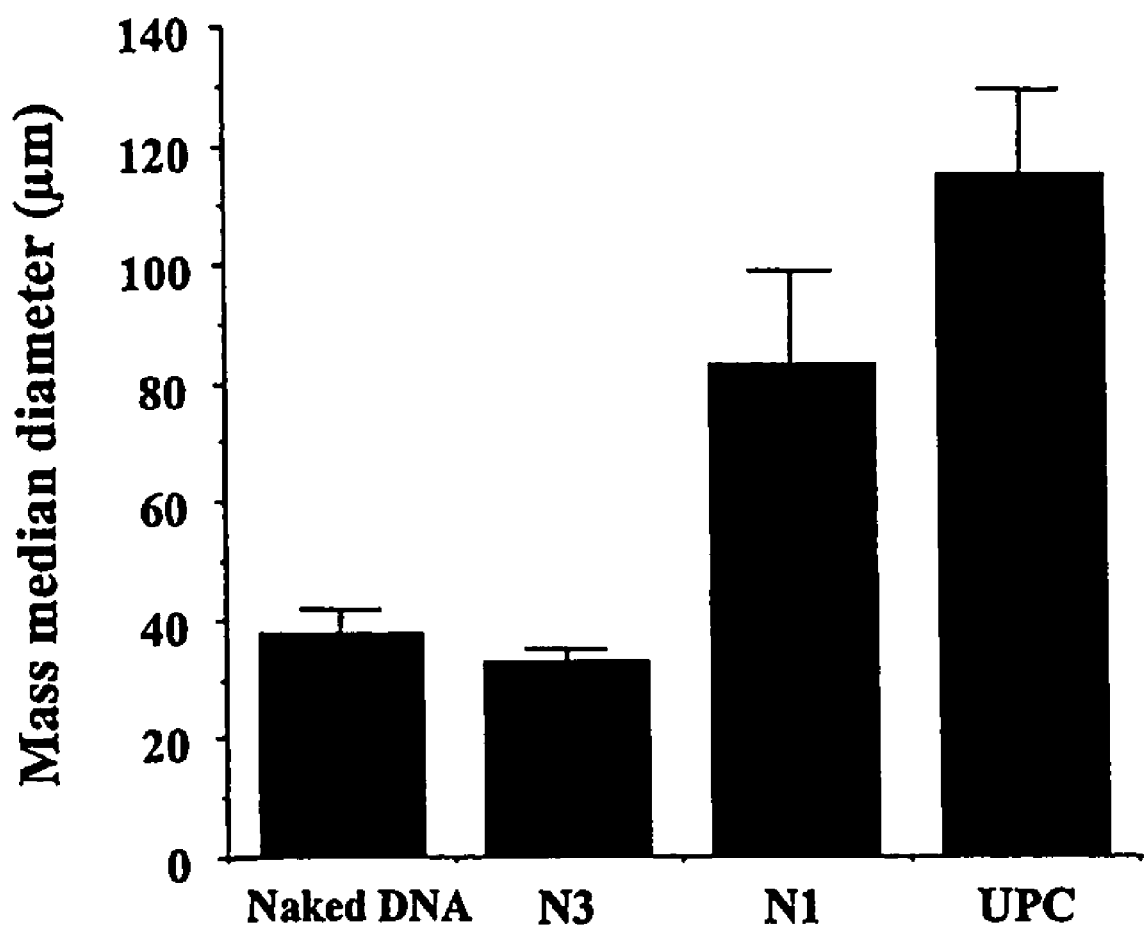

FIG. 13 shows the liquid droplet size (mass median diameter, MMD) after aerosolization of compositions containing cations complexed with pLuc. Fractions of chitosan oligomers containing 15-21 (N3) and 36-50 (N1) monomer units and an ultra pure chitosan, Protasan UPG 210 (UPC), were complexed with pLuc at an amine/phosphate charge ratio of 60:1 (+/−) and 3:1 (+/−), respectively. The MMD was clearly dependent on the composition. The smallest droplet size was obtained with naked pLuc and the composition containing 15-21 monomer units (N3) complexed with pLuc. Statistical differences between mean values were investigated using ANOVA. Differences between group means were considered significant at P<0.05.

Using the expression of a reporter protein, luciferase, as a model for a therapeutic protein in an in vivo lung model, it was found that formulations comprising plasmid DNA and a certain composition of chitosan oligomers having well-defined chain lengths, distribution of chain lengths, and chemical composition, are advantageous to achieve delivery of the nucleic acid into cells of a selected tissue and to obtain in vivo expression of the desired molecules encoded for by the nucleic acids.

It was found that a chitosan oligomer fraction, prepared from chitosan, having a number-average degree of polymerization of 18 ($DP_n$=18, as determined by $^{13}C$-NMR-spectroscopy), showing a relatively narrow size distribution as compared to the Kuhn-distribution and having more than 99% D-units ($F_A$<0.01), formed stable complexes (as revealed by agarose gel electrophoresis) with pLuc at an amine/phosphate charge ratio of 60:1 (+/−). A significantly higher in vivo lung luciferase gene expression was obtained with the polydisperse $DP_n$=18 sample compared to monodisperse chitosan oligomers having 6, 10 and 12 monomer units that formed unstable complexes with pLuc at an amine/phosphate charge ratio of 60:1 (+/−). The fact that stable complexes resulted in a higher gene expression than unstable complexes is in agreement with the prior art (Fischer et al., 1999; Gebhart and Kabanov, 2001; Koping-Hoggard et al., 2001). However, a decrease in luciferase expression was detected with stable complexes formed with chitosan oligomers having higher average molecular sizes than the $DP_n$18 sample. The fraction $DP_n$18 was further fractionated into fractions having more narrow distributions that is 10-14 monomer units (N4), 15-21 monomer units (N3), 22-35 monomer units (N2) and 36-50 monomer units (N1). Complexes between the fraction having 15-21 monomer units and pLuc resulted unexpectedly in the highest in vivo lung gene expression although unstable complexes were formed at an amine/phosphate charge ratio of 60:1 (+/−). The fraction 10-14 monomer units also formed unstable complexes with pLuc and resulted only in a modest luciferase expression.

Also, aerosolisation of complexes between the fraction having 15-21 monomer units and pLuc resulted in comparable droplet sizes as an aerosolised solution of naked pLuc. In contrast, aerosolisation of the fraction having 36-50 monomer units complexed with pLuc and UPC (approximately 1000-mer) complexed with pLuc resulted in a 2 and 3-fold higher droplet size, respectively. This formulation-dependent effect on the droplet size might be explained by an increased viscosity of the solution with increasing molecular weight of the cation, thus producing droplets of a larger size.

EXAMPLES

Example 1

Preparation of Low-Molecular Weight Chitosans

Chitosan Protasan UP G 210 ($F_A$=0.17, weight-average molecular weight of 162,000) was obtained from Pronova Biomedical AS, Oslo, Norway. The low-molecular weight oligomer of N-glucosamine was obtained by chemical depolymerisation of chitosan using $NaNO_2$ and subsequent reduction by $NaBH_4$ as described by Tømmeraas et al., 2001, where the molecular weight was controlled by the amount of $NaNO_2$ relative to the amount of chitosan. The fraction of acetylated units was controlled by heterogeneous deacetylation to obtain $F_A$ of less than 0.001 as determined by proton NMR-spectroscopy as described previously (Vårum et al., 1991). Typically, 1.0 gram of chitosan was dissolved in 100 ml of 2.5% aqueous acetic acid, dissolved oxygen was removed by bubbling nitrogen gas through the solution for 5 minutes, and 5 ml of a freshly prepared solution of $NaNO_2$ in distilled water (10 mg/ml) was added. The reaction was allowed to proceed for 4 hours in darkness, whereafter the depolymerized chitosan was conventionally reduced by adding 3 grams of $NaBH_4$ overnight in darkness. The pH was adjusted to 4.5 using acetic acid. The solution was dialysed (Medicell dialysis tubing, MWCO 12000-14000) three times against 0.2M NaCl and six times against distilled water and lyophilized, to obtain the low-molecular weight oligomer as their hydrochloride salt. Alternatively, the low-molecular weight oligomers were obtained by enzymatic depolymerisation using a chitosanase from *Streptomyceus griseus* (Sigma C 9830 or Sigma C 0794) where the molecular weight is controlled by the amount of enzyme relative to the amount of chitosan and the incubation time. 0.5 gram of chitosan was dissolved at a concentration of 20 mg/ml in 0.1M sodium-acetate/acetic acid buffer (pH 5.5) and 0.65 units of Chitosanase (Sigma C 0794) was added to the chitosan solution and incubated for 18 hours at 37° C. The enzyme reaction was stopped by decreasing the pH to 2 and then boiled for 5 minutes. The depolymerized chitosan was dialysed and lyophilized as described above, to obtain the low molecular weight enzyme-degraded chitosan as their hydrochloride salts.

Example 2

Preparation and Characterization of Fractionated Samples

The low-molecular weight chitosans prepared as described in Example 1 were fractionated by size-exclusion chromatography on two 2.5×100 cm columns connected in series as described previously (Tømmeraas et al., 2001). Fractions of 4 mL were collected and pooled according to the chromatograms shown in FIG. 6 (*a* and *b*), to obtain 4 fractions differing in molecular weight designated

N1 (nitrous acid degraded) or E1 (chitosanase degraded)

N2 (nitrous acid degraded) or E2 (chitosanase degraded)

N3 (nitrous acid degraded) or E3 (chitosanase degraded)

N4 (nitrous acid degraded) or E4 (chitosanase degraded)

TABLE 1

The samples were analyzed by SEC-MALLS, which yielded the following chain length distributions (average of 3 injections):

| Sample | $DP_w$ | $DP_n$ | $DP_w/DP_n$ |
|---|---|---|---|
| Unfractionated N0 (nitrous acid degraded) | 31 | 25 | 1.22 |
| N1 | 44 | 40 | 1.09 |
| N2 | 27 | 26 | 1.03 |
| N3 | 20 | 19 | 1.03 |
| N4 | 14 | 13 | 1.04 |
| Unfractionated E0 (chitosanase degraded) | 27 | 21 | 1.31 |
| E1 | 50 | 44 | 1.12 |
| E2 | 33 | 30 | 1.06 |
| E3 | 25 | 23 | 1.03 |
| E4 | 17 | 16 | 1.07 | wherein DPw = weight average DP
and DPn = number average DP

Example 3

Formulation and In Vivo Lung Gene Expression

A polydisperse cationic chitosan oligomer fraction having a degree of polymerization (DP) between 6-50 (number-average DP of 18 as determined from the non-reducing ends in the $^{13}$C-nmr-spectrum, N0) and well-defined cationic oligomers, having DP's of 6, 10, 12, 10-14 (N4), 15-21 (N3), 22-35 (N2), 36-50 (N1) were prepared from chitosan according to the methods described in Example 1 and Example 2. Firefly luciferase plasmid DNA (pLuc) was purchased from Aldevron, Fargo, N.D., USA. Stock solutions of cationic chitosan oligomers (2 mg/ml) were prepared in sterile distilled deionized water, pH 6.2±0.1 followed by sterile filtration. Complexes between cationic chitosan oligomers and pLuc were formulated at a charge ratio of 60:1 (+/−) by adding cationic oligomer and then pLuc to sterile water under intense stirring on a vortex mixer (Heidolph REAX 2000, KEBO Lab, Spånga, Sweden). After 15 min the complexes were concentrated by mild evaporation under vacuum in a SpeedVac Plus centrifuge (Savant Instruments, Holbrook, N.Y.) for approximately 90 min to obtain pLuc concentrations of around 250 μg/ml) (Koping-Hoggard et al., 2001). In addition, pLuc was formulated with PEI 25 kDa (Aldrich Sweden, Stockholm, Sweden) and an ultra pure chitosan, Protasan UPG 210 (Pronova Biopolymer, Oslo, Norway) at previously optimized conditions, charge ratio 5:1 (+/−) and 3:1 (+/−) respectively (Bragonzi et al., 2000; Koping-Hoggard et al., 2001).

Mice (male Balb/c, 6-8 weeks old, 4 animals per group, Charles River, Uppsala, Sweden) were anesthesized with ketamin/xylazine (5/20 vol %, 0.1 ml/10 g of body weight), and the trachea was surgically exposed with a 0.5 cm long skin incision in the neck. 100 μl of the complexes described aboved was slowly administrated dropwise into the trachea and the mice were sutured. At 72 h after administration, the animals were sacrificed by carbon dioxide and the lungs were surgically removed, washed in PBS and 0.3 ml ice-cold luciferase lysis buffer (Promega, Madison, Wis.) with a protease inhibitor cocktail (Complete, Boehringer Mannheim Scandinavia AB, Bromma, Sweden) was added. The tissue samples were quickly frozen in liquid nitrogen and stored at −80° C. until analysis.

In a cold room, the tissue samples were homogenized in a bead beater (Biospec Products, Inc., OK) followed by centrifugation (Centrifuge 5403, Eppendorf-Nethelar-Hinze GmbH, Hamburg, Germany) at 4° C. and 15,000 rpm for 10 min. An amount of 50 µl of the clear supernatant from each test tube was mixed with 50 µl of luciferase reagent (Promega) and analyzed by a luminometer (Mediators PhL, Vienna, Austria) with an integration time of 8 s. In order to quantify the luciferase expression, a standard curve of luciferase (Sigma, St. Louise, Mo.) was prepared by adding defined amounts of the luciferase standard to the supernatants of homogenized tissues from untreated control animals. The total protein content in each sample was analyzed by the BCA assay (Pierce, Rockford, Ill.) and quantified using BSA (bovine serum albumin) as a reference protein. The absorbance was measured at 540 nm on a microplate reader (Multiscan MCC/340, Labsystems Oy, Helsinki, Finland).

Results of the gene transfection efficiency in mouse lungs 72 h after administration of pLuc complexed with cationic chitosan oligomers of various degree of polymerization (molecular weight) are shown in FIG. 9. Surprisingly, the significantly highest luciferase expression was obtained with pLuc complexed with a chitosan oligomer N0 having 18 as the number average degree of polymerization.

The results of the gene transfection efficiency in mouse lungs 72 h after administration of pLuc complexed with cationic chitosan oligomers of various degree of polymerization (molecular weight) are shown in FIG. 10. The chitosan oligomer N0 having 18 as the number average degree of polymerization was fractionated, as described in Example 2, into four samples having well-defined and narrow distributions of their degrees of polymerization. Surprisingly, the fraction containing chitosan oligomers having chain lengths between 15-21 monomer units (N3), showed higher gene expression than PEI and significantly higher gene expression compared to the un-fractionated sample N0 having 18 as the number average degree of polymerization.

The results of the agarose gel retardation assay are shown in FIG. 11. With increasing molecular weight (degree of polymerization) of the chitosan oligomer, the stability of formed complexes increases. Thus, almost complete retention of pLuc was detected with complexes formed with the fractions containing 22-35 (N2) and 36-50 (N1) monomer units as compared to complexes formed with 10-14 (N4) and 15-21 (N3) monomer units. The unfractionated sample N0 having 18 as the number average degree of polymerization also formed stable complexes with pDNA. A higher in vivo gene expression (FIG. 10) was surprisingly obtained with the less stable 15-21 (N3) complexes compared to the stable complexes formed with DPn18 (N0).

Example 4

In vitro Gene Expression

Two different batches of fractionated low molecular weight cationic chitosan oligomers; N1 and E1, as described in example 2 and prepared 9 months apart, and commercial chitosan (Protasan UPG 210, batch 1: apparent viscosity of 70 mPas, batch 2: apparent viscosity of 146 mPas) ordered 3 years apart were complexed with pLuc at charge ratios of 10:1 (+/−) and 2.4:1 (+/−), respectively, as described in Example 2. Stable pDNA complexes were used.

24 h before transfection, the epithelial human embryonic kidney cell line 293 (ATCC, Rockville, Md., USA) were seeded at 70% confluence in 96-well tissue culture plates (Costar, Cambridge, UK). Prior to transfection, the cells were washed and then 50 µl (corresponding to 0.33 µg pLuc) of the polyplex formulations was added per well. After 5 h incubation, the formulations were removed and 0.2 ml of fresh culture medium was added. The medium was changed every second day for experiments exceeding two days. At 96 h and 144 h, cells were washed with PBS (pH 7.4), lysed (Promega) and luciferase gene expression was measured with a luminometer (Mediators PhL). The amount of luciferase expressed was determined from a standard curve prepared with firefly luciferase (Sigma) and total cell protein was determined using the bichinchoninic acid test (Pierce).

The results of the luciferase gene expression in vitro after incubating 293 cells with two batches of fractionated low molecular weight cationic chitosan oligomers; N1 and E1 and commercial chitosan Protasan UPG 210, respectively, are shown in FIG. 12. The gene expression varied 10-fold between the two batches of Protasan UPG 210 but not significantly between the two batches of the fractionated low molecular weight cationic chitosan oligomers N1 and E1.

Example 5

Droplet Size after Aerosilisation

Complexes between cationic chitosan oligomers and pLuc were prepared as described in Example 3 to obtain pLuc concentrations of 500 µg/ml. As a control, an ultra pure chitosan (UPC, degree of polymerization around 1000) complexed with pLuc were used at optimal conditions, charge ratio 3:1 (+/−) (Koping-Hoggard et al., 2001). Aerosols containing complexes between cationic chitosan oligomers and pLuc were produced with the use of a nebulization catheter (Trudell Medical International, London Ontario, Canada) containing liquid- and gas (air)-channels. Firstly, 100 µl of the complex solution was loaded into a liquid reservoir coupled to the nebulization catheter (liquid inlet). Then, to obtain aerosols, pulses of pressurized air (3.5 bar) was applied for short time periods over the liquid reservoir (20 ms) and the gas channels of the nebulization catheter (50 ms). The droplet size of produced aerosols was measured with a Mastersizer X (Malvern instruments Ltd., Malvern, UK).

The liquid droplet size (mass median diameter, MMD) after aerosolisation of compositions containing cations complexed with pLuc are shown in FIG. 13. The MMD was clearly dependent on the composition. The smallest droplet size was obtained with "naked" pLuc and the composition containing 15-21 monomer units (N3) complexed with pLuc.

REFERENCES

Artursson P, Lindmark T, Davis S S and Illum L (1994) Effect of chitosan on the permeability of monolayers of intestinal epithelial cells (Caco-2). *Pharm Res* 11:1358-1361.

Boussif O, Lezoualch F, Zanta M A, Mergny M D, Scherman D, Demeneix B and Behr J P (1995) A versatile vector for gene and oligo nucleotide transfer into cells in culture and in vivo: Polyetylenimine. *Proceedings of the National Academy of Sciences USA* 92:7297-7301.

Bragonzi A, Dina G, Villa A, Calori G, Biffi A, Bordignon C, Assael B M and Conese M (2000) Biodistribution and transgene expression with non-viral cationic vector/DNA complexes in the lungs. *Gene Ther* 7:1753-1760.

Deshpande D, Blezinger P, Pillai R, Duguid J, Freimark B and Rolland A (1998) Target specific optimization of cationic lipid-based systems for pulmonary gene therapy. *Pharm Res* 15:1340-1347.

Felgner J H, Kumar R, Sridhar C N, Wheeler C J, Tsai Y J, Border R, Ramsey P, Martin M and Felgner P L (1994) Enhanced gene delivery and mechanism studies with a novel series of cationic lipid formulations. *Journal of Biological Chemistry* 269:2550-2561.

Ferrari S, Moro E, Pettenazzo A, Behr J, Zacchello F and Scarpa M (1997) ExGen 500 is an efficient vector for gene delivery to lung epithelial cells in vitro and in vivo. *Gene Therapy* 4:1100-1106.

Fischer D, Bieber T, Li Y, Elsasser H P and Kissel T (1999) A novel non-viral vector for DNA delivery based on low molecular weight, branched polyethylenimine: effect of molecular weight on transfection efficiency and cytotoxicity. *Pharm Res* 16:1273-1279.

Florea B, Thanou, M., Geldof, M., Meaney, C., Junginger, H. E. and Borchard, G. (2001) Modified chitosan oligosaccharides and polyethylenimine as transfection agents for gene therapy in cystic fibrosis. *Journal*

Gautam A, Densmore C L, Golunski E, Xu B and Waldrep J C (2001) Transgene expression in mouse airway epithelium by aerosol gene therapy with PEI-DNA complexes. *Mol Ther* 3:551-556.

Gautam A, Densmore C L, Xu B and Waldrep J C (2000) Enhanced gene expression in mouse lung after PEI-DNA aerosol delivery. *Mol Ther* 2:63-70.

Gebhart C L and Kabanov A V (2001) Evaluation of polyplexes as gene transfer agents. *J Control Release* 73:401-416.

Godbey W T, Wu K K and Mikos A G (1999) Size matters: Molecular weight affects the efficiency of poly(ethylenimine) as a gene delivery vehicle. *J Biomed Mater Res* 45:268-275.

Godbey W T, Wu K K and Mikos A G (2001) Poly(ethylenimine)-mediated gene delivery affects endothelial cell function and viability. *Biomaterials* 22:471-480.

Griesenbach U. Chonn A, Cassady R, Hannam V, Ackerley C, Post M, Tanswell A K, Olek K, O'Brodovich H and Tsui L C (1998) Comparison between intra tracheal and intravenous administration of liposome-DNA complexes for cystic fibrosis lung gene therapy. *Gene Ther* 5:181-188.

Hudde T, Rayner S A, Comer R M, Weber M, Isaacs J D, Waldmann H, Larkin D F and George A J (1999) Activated polyamidoamine dendrimers, a non-viral vector for gene transfer to the corneal endothelium. *Gene Ther* 6:939-943.

Illum L (1998) Chitosan and its use as a pharmaceutical excipient. *Pharm Res* 15:1326-1331.

Koping-Hoggard M, Melnikova, Y., Varum K. M., Lindman, B. and Artursson, P. (2001) Chitosan polyplexes as a gene delivery system. Characterization of structure-activity relationships from supramolecular shape. Unpublished Koping-Hoggard M, Tubulekas I, Guan H, Edwards K, Nilsson M, Varum K and Artursson P (2001) Chitosan as a non-viral gene delivery system. Structure-property relationships and characteristics compared with polyethylenimine in vitro and after lung administration in vivo. *Gene Ther* 8:1108-1121.

Ledley F D (1996) Pharmaceutical approach to somatic gene therapy. *Pharm Res* 13:1595-1614.

Li S and Huang L (1997) In vivo gene transfer via intravenous administration of cationic lipid-protamine-DNA (LPD) complexes. *Gene Ther* 4:891-900.

Li S, Tan Y, Viroonchatapan E, Pitt B R and Huang L (2000) Targeted gene delivery to pulmonary endothelium by anti-PECAM antibody. *Am J Physiol Lung Cell Mol Physiol* 278:L504-511.

Luo D and Saltzman W M (2000) Synthetic DNA delivery systems. *Nat Biotechnol* 18:33-37.

MacLaughlin F C, Mumper R J, Wang J, Tagliaferri J M, Gill I, Hinchcliffe M and Rolland A P (1998) Chitosan and depolymerized chitosan oligomers as condensing carriers for in vivo plasmid delivery [In Process Citation]. *J Controlled Release* 56:259-272.

Mumper R J, Duguid J G, Anwer K, Barron M K, Nitta H and Rolland A P (1996) Polyvinyl derivatives as novel interactive polymers for controlled gene delivery to muscle. *Pharm Res* 13:701-709.

Mumper R J, Wang J, Klakamp S L, Nitta H, Anwer K, Tagliaferri F and Rolland A P (1998) Protective interactive noncondensing (PINC) polymers for enhanced plasmid distribution and expression in rat skeletal muscle. *J Control Release* 52:191-203.

Ottøy M H, Vårum K M, Christensen B E, Anthonsen M W & Smidsrød O (1996) Preparative and analytical size-exclusion chromatography of chitosans. *Carbohydr. Polym.* 31:253-261.

Plank C, Tang M X, Wolfe A R and Szoka F C, Jr. (1999) Branched cationic peptides for gene delivery: role of type and number of cationic residues in formation and in vitro activity of DNA polyplexes [published erratum appears in Hum Gene Ther 1999 Sep. 1; 10(13):2272]. *Hum Gene Ther* 10:319-332.

Putnam D, Gentry C A, Pack D W and Langer R (2001) Polymer-based gene delivery with low cytotoxicity by a unique balance of side-chain termini. *Proc Natl Acad Sci USA* 98:1200-1205.

Roberts, G. A. F., "Chitin Chemistry" (1992), Macmillan, London, page 6-7.

Roy K, Mao H Q, Huang S K and Leong K W (1999) Oral gene delivery with chitosan-DNA nanoparticles generates immunologic protection in a murine model of peanut allergy. *Nat Med* 4:387-391.

Saeki Y, Matsumoto N, Nakano Y, Mori M, Awai K and Kaneda Y (1997) Development and characterization of cationic liposomes conjugated with HVJ (Sendai virus): reciprocal effect of cationic lipid for in vitro and in vivo gene transfer. *Hum Gene Ther* 8:2133-2141.

Sato T, Ishii T and Okahata Y (2001) In vitro gene delivery mediated by chitosan. effect of pH, serum, and molecular mass of chitosan on the transfection efficiency. *Biomaterials* 22:2075-2080.

Song Y K, Liu F, Chu S and Liu D (1997) Characterization of cationic liposome-mediated gene transfer in vivo by intravenous administration. *Hum Gene Ther* 8:1585-1594.

C. Tanford (1961) Physical chemistry of macromolecules, John Wiley and Sons, New York, Section 8b and 33a)

Tømmeraas K, Varum K M, Christensen B E and Smidsrod O (2001) Preparation and characterisation of oligosaccharides produced by nitrous acid depolymerisation of chitosans. *Carbohydr Res* 333:137-144.

Vårum K M, Anthonsen M W, Grasdalen H and Smidsrod O (1991) Determination of the degree of N-acetylation and the distribution of N-acetyl groups in partially N-deacetylated chitins (chitosans) by high-field n.m.r. spectroscopy. *Carbohydr Res* 211:17-23.

Vårum, K M, Ottøy, M H and Smidsrød, O (2001) Acid hydrolysis of chitosans. *Carbohydr. Polym.* 46:89-98.

Wolff J A, Malone R W, Williams P, Chong W, Acsadi G, Jani A and Felgner P L (1990) Direct gene transfer into mouse muscle in vivo. *Science* 247:1465-1468.

The invention claimed is:

1. A composition comprising complexes of:
   (a) cationic chitosan oligomers obtained from cationic polysaccharide chitosan by depolymerization wherein said cationic chitosan oligomers have: (i) an average degree of polymerization of $DP_n=18$; (ii) 15-21 monomer units; and (iii) a fraction of N-acetylated units ($F_A$) of 0-0.01; and
   (b) a nucleic acid.

2. The composition of claim 1, wherein said depolymerization is a chemical or enzymatic method.

3. The composition of claim 1, wherein said composition has a net positive charge ratio.

4. The composition of claim 1, wherein said nucleic acid comprises a coding sequence that will express its function when said nucleic acid is introduced into a host cell.

5. The composition of claim 4, wherein said nucleic acid is selected from the group consisting of DNA and RNA molecules.

6. The composition of claim 5, wherein said composition has a pH in the range of 3.5 to 8.

7. A method of preparing the composition of claim 1, comprising the steps of:
   (a) exposing said cationic chitosan oligomer to an aqueous solvent;
   (b) mixing the aqueous solution of step (a) with said nucleic acid in an aqueous solvent; and
   (c) reducing the volume of the product solution obtained in step (b) to achieve a desired concentration of the said composition.

8. A method of administering nucleic acid to a mammal, using the composition of claim 1, and introducing the composition into the mammal.

9. The method of claim 8, wherein the composition is introduced into the mammal by administration to mucosal tissues by pulmonary, nasal, oral, buccal, sublingual, rectal or vaginal routes.

10. The method of claim 8, wherein the composition is introduced into the mammal by administration to submucosal tissues by parenteral routes that is intravenous, intramuscular, intradermal, subcutaneous or intracardiac administration, or to internal organs, blood vessels or other body surfaces or cavities exposed during surgery.

11. The method of claim 8, whereby said nucleic acid is capable of expressing its function inside said cell.

12. The use of the composition of claim 1, in the manufacture of a medicament for prophylactic or therapeutic treatment of a mammal, or in the manufacture of a diagnostic agent for use in in vivo or in vitro diagnostic methods.

13. The use of the composition of claim 12 in the manufacture of a medicament for use in gene therapy, antisense therapy, or genetic vaccination for prophylactic or therapeutic treatment of malignancies, autoimmune diseases, inherited disorders, pathogenic infections and other pathological diseases.

* * * * *